US011311673B2

(12) United States Patent
Cowe

(10) Patent No.: US 11,311,673 B2
(45) Date of Patent: Apr. 26, 2022

(54) PACKAGING AND DEVICES FOR MIXING MEDICAMENT SUBSTANCES

(71) Applicant: Owen Mumford Limited, Oxfordshire (GB)

(72) Inventor: Toby Cowe, Oxfordshire (GB)

(73) Assignee: Owen Mumford Limited, Oxford (GB)

(*) Notice: Subject to any disclaimer, the term of this patent is extended or adjusted under 35 U.S.C. 154(b) by 349 days.

(21) Appl. No.: 16/462,038

(22) PCT Filed: Nov. 17, 2017

(86) PCT No.: PCT/GB2017/053465
§ 371 (c)(1),
(2) Date: May 17, 2019

(87) PCT Pub. No.: WO2018/091912
PCT Pub. Date: May 24, 2018

(65) Prior Publication Data
US 2019/0298926 A1  Oct. 3, 2019

(30) Foreign Application Priority Data
Nov. 18, 2016 (GB) ...................................... 1619553

(51) Int. Cl.
*A61M 5/24* (2006.01)
*A61M 5/19* (2006.01)
(Continued)

(52) U.S. Cl.
CPC ............ *A61M 5/2448* (2013.01); *A61M 5/19* (2013.01); *A61M 5/284* (2013.01);
(Continued)

(58) Field of Classification Search
CPC ...... A61M 5/2448; A61M 5/19; A61M 5/284; A61M 5/3158; A61M 5/31596;
(Continued)

(56) References Cited

U.S. PATENT DOCUMENTS 3,735,761 A * 5/1973 Hurschman ........... A61M 5/284
604/88
4,689,042 A * 8/1987 Sarnoff ............... A61M 5/2066
604/89

(Continued)

FOREIGN PATENT DOCUMENTS

EP      2 422 761 A1    2/2012
WO   WO 03/074103 A2   9/2003

OTHER PUBLICATIONS

May 9, 2018 International Search Report for PCT/GB2017/053465.
May 9, 2018 Written Opinion of Int'l Searching Authority for PCT/GB2017/053465.

*Primary Examiner* — Brandy S Lee
*Assistant Examiner* — Hong-Van N Trinh
(74) *Attorney, Agent, or Firm* — Quarles & Brady LLP

(57) ABSTRACT

A device (200) for mixing first and second substances. The device comprises a first container (100) for storage of the first substance and a second container (150) received in the first container (100) and for storage of the second substance. An outlet (112) is disposed at the distal end of the first container (100). Valve means (180) are provided for closing a distal end of the second container (150) and a proximal end of the first container (100). A stopper means (166) closes a proximal end of the second chamber (152) and is movable with respect to the second container (150). An operating mechanism drives relative movement between the first and second containers for causing displacement of the second substance into the first chamber (102) through the valve means (180) when the outlet (112) is closed, for mixing the first and second substances in a mixing stroke of the device.

7 Claims, 11 Drawing Sheets

(51) Int. Cl.
   *A61M 5/28*     (2006.01)
   *A61M 5/315*    (2006.01)
   *A61M 5/31*     (2006.01)
(52) U.S. Cl.
   CPC ...... *A61M 5/3158* (2013.01); *A61M 5/31596* (2013.01); *A61M 2005/2407* (2013.01); *A61M 2005/2437* (2013.01); *A61M 2005/3128* (2013.01); *A61M 2005/31598* (2013.01)
(58) Field of Classification Search
   CPC ........... A61M 2005/31598; A61M 2005/2407; A61M 2005/2437; A61M 2005/3128; A61M 5/2429; A61M 5/2066
   See application file for complete search history.

(56) References Cited

U.S. PATENT DOCUMENTS

| | | | |
|---|---|---|---|
| 4,755,169 A | | 7/1988 | Sarnoff et al. |
| 5,569,193 A | * | 10/1996 | Hofstetter ......... A61M 5/31596 604/89 |
| 5,876,372 A | | 2/1999 | Grabenkort et al. |

* cited by examiner

PACKAGING AND DEVICES FOR MIXING MEDICAMENT SUBSTANCES

The present application is a § 371 submission of international application no. PCT/GB2017/053465, filed 17 Nov. 2017 and titled Packaging and Devices for Mixing Medicament Substances, which was published in the English language on 24 May 2018 with publication no. WO 2018/091912 A1, and which claims the benefit of the filing date of GB 16 19553.9 filed 18 Nov. 2016, the contents of which are incorporated herein by reference.

This invention relates to packaging and devices suitable for mixing medicament substances. In particular, but not exclusively, the invention relates to cartridge-type primary packaging for constituents of reconstitutable medicaments and devices for use with the primary packaging. This invention further relates to medicaments, including pharmaceutical compositions, for subcutaneous injection or infusion disposed within the delivery devices and methods of treating patients with conditions susceptible to treatment by delivering the medicament using the delivery devices described herein.

Medicaments for subcutaneous injection or infusion are used in therapy in various different clinical situations. In some cases, it is necessary or advantageous to supply a medicament to a user as two separate components, and to mix the components just prior to use.

For instance, some injectable medicaments, such as blood factors for the treatment of haemophilia and glucagon for the treatment of severe hypoglycemia, have an unacceptably short shelf-life when in liquid form, and are therefore most commonly supplied in freeze-dried or lyophilised form as a solid powder. In the lyophilised form, the shelf life of the medicament is substantially extended. Prior to use, the medicament must be reconstituted by mixing with a suitable sterile diluent, such as water or saline.

In a conventional arrangement, the solid component of a medicament is supplied in a vial, and the liquid diluent is supplied in a separate syringe. The vial is typically closed with a polymeric membrane or septum that can be pierced by a needle of the syringe. In use, the syringe needle is inserted through the septum, and the diluent is injected into the vial to mix with the solid component. The vial is then shaken to encourage thorough mixing. The syringe may be removed from the vial during shaking, and so the septum is typically self-sealing to prevent leakage of the vial contents once the needle is withdrawn.

After reconstitution of the medicament, the syringe is re-inserted in the vial if necessary and then the mixture is drawn into the syringe. The syringe, now containing the reconstituted medicament, is removed from the vial and can be used to administer the reconstituted medicament to a patient by injection.

This conventional arrangement has several disadvantages. The need to provide a separate vial and syringe, and to keep those components sterile, can be inconvenient. Also, the number of steps involved and the relatively complex actions required can make the arrangement unattractive in some clinical situations, such as self-administration by a patient at home. Self-administration can be particularly difficult for young patients, or those with reduced manual dexterity.

In the field of single-component, non-reconstitutable liquid medicaments, the problem of providing medicaments in a more convenient form for injection has been addressed by the development of several different types of medicament delivery device.

For example, the need for a separate vial and syringe can be avoided by the use of pre-filled, disposable syringes containing a single dose of the medicament. In one common pre-filled syringe design, sold under the registered trade mark Hypak (Becton Dickinson, N.J., USA), a needle is permanently fixed to the distal end of the syringe body, and the needle is kept sterile by a removable cap. In other examples, a pre-filled syringe body is provided with a suitable connection for a needle, such as a Luer connector.

More sophisticated auto-injector devices designed for self-administration of a single, fixed dose of non-reconstitutable medicament are also known. Typically, in such devices, one or more of needle insertion, medicament delivery, dose indication, needle retraction and deployment of a needle shield after injection are triggered by one or more user operations, such as operating a trigger button or slider. The medicament dose in an auto-injector device may be provided in the form of a disposable, pre-filled glass syringe with a fixed needle, such as a Hypak syringe of the type described above, or in a cartridge or other package.

Other known single-component medicament delivery devices include safety syringes, injection pens, infusion pumps and so on. In these cases, the medicament may be contained in cartridges or other packages that are specifically designed for the device.

In contrast, relatively few devices suitable for the delivery of reconstitutable medicaments are available. One particular challenge in this respect is the design of a suitable primary packaging, since it is necessary to keep the two components apart until the device is used, and to enable mixing of the medicaments before delivery. Another problem is providing a device that is simple and intuitive to operate. In particular, some known devices rely on the user to manipulate the device to perform several steps in sequence, increasing the risk of incorrect operation.

U.S. Pat. No. 4,755,169 describes an auto-injector device having a first container for a dry substance and a second container for a diluent. Each container is in the form of a syringe having a needle at a first, distal end and a slidable bung or stopper to seal the second, proximal end of the respective container. The second container is arranged telescopically in the first container, such that, when the stopper of the second container is moved distally by a drive mechanism of the device, the needle of the second container pierces the stopper of the first container, thereby allowing the diluent in the second container to flow into the first container to mix with the dry substance. In this example, and in other known devices for mixing medicaments before delivery, the primary packaging is relatively complex and is designed specifically for use only in the described device.

It would, however, be desirable to provide primary packaging that can be used in multiple different types of delivery device without modification of the packaging. For example, to ensure compatibility and safety of primary packages, it is necessary to test and validate every combination of medicament and primary packaging that is released to the market. The validation process may involve clinical trials and regulatory approval, and may therefore be extremely expensive and time-consuming. In some cases, the cost of validating a new primary package for an existing medicament may be prohibitive. In other cases, where a new dedicated primary package for a new device is developed, the increased medicament cost may discourage the approval of new devices by healthcare funding bodies or insurers.

Accordingly, it is an object of the invention to provide a simple primary packaging that is suitable for a reconstitutable medicament and that can be used with multiple different types of delivery device to suit different clinical situations. It is a further object of the invention to provide simple and reliable devices in which mixing of the constituent parts of a reconstitutable medicament can be performed automatically during an operating sequence of the device with a minimum number of user steps. A further object of the invention is to provide medicaments, including pharmaceutical compositions, for subcutaneous injection or infusion disposed within the delivery devices and methods of treating patients with conditions susceptible to treatment by delivering the medicament using the delivery devices described herein.

According to a first aspect of the invention, a device is provided for mixing first and second substances in a cartridge comprising a first container having a first chamber for storage of a first substance, an outlet disposed at the distal end of the first chamber, closure means for closing the outlet, a second container at least partially received in the first container and having a second chamber for storage of a second substance, valve means for closing a distal end of the second chamber and a proximal end of the first chamber, and stopper means for closing a proximal end of the second chamber, the stopper means being movable with respect to the second container. The device comprises a cartridge holder for receiving the cartridge, and an operating mechanism for driving relative movement between the first container and the second container to displace the second substance into the first chamber through the valve means when the outlet is closed to cause mixing of the first and second substances in a mixing stroke of the device.

The device may have one of two different configurations for performing the mixing stroke.

In the first configuration, the operating mechanism drives relative movement between the first container and the second container so as to reduce the pressure in the first chamber, thereby to cause displacement of the second substance into the first chamber through the valve means when the outlet is closed for mixing the first and second substances in the mixing stroke of the device.

In this first configuration, the operating mechanism may be arranged for driving movement of the second container in the proximal direction with respect to the cartridge holder. Alternatively, the operating mechanism may be arranged for driving movement of the first container in the distal direction with respect to the cartridge holder. In either case, a mixing drive element may be provided, and the operating mechanism may be arranged for driving movement of the mixing drive element with respect to the cartridge holder to cause relative movement between the first container and the second container upon activation of the operating mechanism.

With these arrangements, the first and second substances can be mixed automatically upon activation of the operating mechanism, for example by the user. Furthermore, the mixing stroke requires relative movement of the containers in only one direction, so that a simple device design can be employed and a separate action to open the valve means is not required.

When provided, the mixing drive element may be moveable in the proximal direction with respect to the cartridge holder to cause movement of the second container in the proximal direction with respect to the housing. The mixing drive element may be further operable to cause movement of the second container in the distal direction with respect to the first container when the outlet is open to displace the mixed first and second substances through the outlet in a delivery stroke of the device. For example, the mixing drive element may be further moveable in the distal direction to cause movement of the second container in the distal direction in the delivery stroke of the device. The mixing drive element may thus for example comprise a button, such as for manual operation by a user during the delivery stroke. Conveniently, proximal movement of the second container during the mixing stroke may cause movement of the mixing drive element from an initial position into an operating position disposed proximally with respect to the initial position. When in the operating position, the mixing drive element can be further displaced to drive the delivery stroke of the device.

The mixing drive element may be attachable to the second container of the cartridge. For example, the device may include a clamp arrangement for securing the drive element to the second container. The clamp arrangement may be arranged to apply a clamping force to an inner wall of the second container. Where the first container is moved in the distal direction with respect to the second container during the mixing stroke, a similar clamp arrangement may be provided for attaching the mixing drive element to the first container.

In a device of the first configuration, the stopper means may be free to move in the distal direction with respect to the second container during the mixing stroke as the volume of the second chamber decreases and the volume of the first chamber increases. To allow free movement of the stopper means, the mixing drive element and/or the clamp arrangement may comprise vent means to admit air to the second container on a proximal side of the stopper means.

In the second configuration, the device can be arranged to move the stopper means in the distal direction with respect to the first and/or second containers. This causes a pressure increase in the second chamber to drive the flow of the second substance into the first chamber. Accordingly, in a device of the second configuration, a mixing drive element is provided, and the operating mechanism is arranged for driving movement of the mixing drive element in the distal direction with respect to the cartridge holder upon operation of the operating mechanism, thereby to cause relative movement between the first container and the second container to displace the second substance into the first chamber through the valve means when the outlet is closed to cause mixing of the first and second substances in the mixing stroke. The device of the second configuration further comprises a delivery drive element that is operable to cause movement of the second container in the distal direction with respect to the first container when the outlet is open to displace the mixed first and second substances through the outlet in a delivery stroke of the device.

As in the first configuration, in a device of this second configuration the first and second substances can be mixed automatically upon activation of the operating mechanism, for example by the user. The delivery drive element can be operated independently of the mixing drive element to perform the delivery stroke after the mixing stroke.

In this second configuration, the mixing drive element may be arranged to displace the stopper means of the cartridge in the distal direction with respect to the second container during the mixing stroke. To this end, the mixing drive element may comprise a plunger. The delivery drive element may comprise a button or may be coupled to a button. Movement of the mixing drive element in the distal direction may cause proximal movement of the second container with respect to the cartridge holder. Preferably, proximal movement of the second container during the mixing stroke of the device causes movement of the delivery drive element from an initial position into an operating position disposed distally with respect to the initial position.

The delivery drive element may be attachable to the second container of the cartridge. A clamp arrangement may be provided for securing the delivery drive element to the second container. For example, the clamp arrangement may be arranged to apply a clamping force to an outer wall of the second container. In another example, the delivery drive element comprises a spring that acts directly on the second container of the cartridge.

In either configuration, the device may be an adaptor for a medicament delivery device, such as an injection pen. In this case, the mixing stroke may be performed by activation of the operating mechanism prior to the adaptor and cartridge being fitted to the medicament delivery device.

The device could instead itself be a medicament delivery device. To that end, the device may be further operable to cause the second container to move in the distal direction with respect to the first container when the outlet is open to displace the mixed first and second substances through the outlet in a delivery stroke of the device. Medicaments, including pharmaceutical compositions, contemplated for use in the delivery device may comprise small molecules, vaccines, live or attenuated cells, oligonucleotides, DNA, peptides, antibodies, and recombinant or naturally occurring proteins, whether human or animal, useful for prophylactic, therapeutic or diagnostic application. The active ingredient can be natural, synthetic, semi-synthetic or derivatives thereof. A wide range of active ingredients are contemplated. These include, for example, hormones, cytokines, hematopoietic factors, growth factors, antiobesity factors, trophic factors, anti-inflammatory factors, and enzymes. The pharmaceutical compositions also may include, but are not limited to, insulin, gastrin, prolactin, human growth hormone (hGH), adrenocorticotropic hormone (ACTH), thyroid stimulating hormone (TSH), luteinizing hormone (LH), follicle stimulating hormone (FSH), human parathyroid hormone (PTH), glucagon, glucagons-like peptide 1 (GLP-1), glucagons-like peptide 2 (GLP-2), insulin-like growth factors (IGFs) such as insulin growth factor I (IGF I), insulin growth factor II (IGF II), growth hormone-releasing factor (GRF), human chorionic gonadotropin (HCG), gonadotropin-releasing hormone, motilin, interferons (alpha, beta, gamma), interleukins (e.g., IL-1, IL-2, IL-4, IL-5, IL-6, IL-9, IL-11, IL-12, IL-13, IL-15, IL-16, IL-17, IL-18, IL-20 or IL-21), interleukin-1 receptor antagonists (IL-Ira), tumor necrosis factor (TNF), tumor necrosis factor-binding protein (TNF-bp), CD40L, CD30L, erythropoietin (EPO), plasminogen activator inhibitor 1, plasminogen activator inhibitor 2, von Willebrandt factor, thrombopoietin, angiopoietin, granulocyte-colony stimulating factor (G-CSF), stem cell factor (SCF), leptin (OB protein), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), transforming growth factors, epidermal growth factor (EGF), vascular endothelial growth factor (VEGF), macrophage colony stimulating factor (M-CSF), granulocyte macrophage colony stimulating factor (GM-CSF), megakaryocyte derived growth factor (MGDF), keratinocyte growth factor (KGF), platelet-derived growth factor (PGDF), novel erythropoiesis stimulating protein (NESP), bone morphogenetic protein (BMP), superoxide dismutase (SOD), tissue plasminogen activator (TPA), pro-urokinase, urokinase, streptokinase, kallikrein, a protease inhibitor e.g. aprotinin, an enzyme such as asparaginase, arginase, arginine deaminase, adenosine deaminase, ribonuclease, catalase, uricase, bilirubin oxidase, trypsin, papain, alkaline phosphatase, glucuronidase, purine nucleoside phosphorylase or batroxobin, an opioid, e.g. endorphins, enkephalins or non-natural opioids, a neuropeptide, neuropeptide Y, calcitonin, cholecystokinin, corticotrophin-releasing factor, vasopressin, oxytocin, antidiuretic hormones, thyrotropin releasing hormone, relaxin, peptideYY, pancreastic polypeptide, CART (cocaine and amphetamine regulated transcript), a CART related peptide, perilipin, melanocortins (melanocyte-stimulating hormones) such as MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins, and human antibodies and humanized antibodies, and other pharmaceutical compositions suitable for administration with the delivery devices. The term proteins, as used herein, includes peptides, polypeptides, consensus molecules, analogs, derivatives or combinations thereof.

The pharmaceutical compositions also may include therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase); antiplatelet (aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); nitric oxide donors; anti-sense olgio nucleotides and combinations thereof.

The pharmaceutical compositions include any extended half-life variants of active ingredients contained therein or analogues thereof. Thus, the active ingredients can be any long acting variants of the active ingredient listed herein or analogues thereof. In some embodiments, the active ingredient includes any extended half-life or long acting variants of hGH, insulin, glucagon, glucagons-like peptide 1 (GLP-1), glucagons-like peptide 2 (GLP-2), insulin-like growth factors (IGFs). In some embodiments, the active ingredient is an extended half-life or long acting variant of hGH. Examples of extended half-life or long acting variants of hGH include, but are not limited to LB03002, NNC126-0883, NNC0195-0092, MOD-4023, ACP-001, Albutropin, somavaratan (VRS-317), and profuse GH.

The mixing drive element may be biased for movement with respect to the cartridge holder. For example, the operating mechanism may comprise a spring for biasing the mixing drive element. Alternatively, the mixing drive element could itself comprise a spring or other biasing means for driving relative movement between the first and second containers during the mixing stroke. More generally, the device may comprise mixing drive means for driving relative movement between the first and second containers during the mixing stroke of the device. Conveniently, the drive means comprises a compression spring, although other types of springs or drive means could be used.

The operating mechanism may be arranged to block relative movement of the first and second containers, and to allow relative movement between the first and second containers to start the mixing stroke. For example, the operating mechanism may comprise a latch mechanism for holding the mixing drive element in an initial position and for releasing the mixing drive element for movement with respect to the cartridge holder upon release of the latch mechanism to start the mixing stroke of the device. In embodiments, the latch mechanism is releasable in response to operation of an operating member, such as upon turning movement of an operating member of the device, which may comprise the mixing drive element or the delivery drive element, relative to the cartridge holder. In another embodiment, the latch mechanism is releasable upon removal of a user-removable component, such as a tab, a cap, a sleeve, or any other suitable component. In these ways, the operating mechanism can be activated by a simple user action.

When present, the latch arrangement may latch the mixing drive element or the delivery drive element, as appropriate, to a housing part of the device, such as the cartridge holder. When both a mixing drive element and a delivery drive element are provided, such as in the second configuration of the device, the latch arrangement may latch the mixing drive element to the delivery drive element.

The closure means of the cartridge may comprise a sealing element. In this case, the device preferably comprises sealing element release means arranged to cooperate with the sealing element of the cartridge to open the outlet. The sealing element release means may, for example, comprise a piercing member, which may form one end of a double-ended needle or which may be a separate tubular component for fluid communication with a needle, cannula or chamber. The device may be arranged to couple with the cartridge in a first attachment position in which the outlet of the cartridge remains closed and a second attachment position in which the sealing element release means cooperates with the sealing element of the cartridge to open the outlet.

The sealing element release means may comprise a sealing element release member. The release member may be generally tubular to define a passage for the flow of medicament. In some embodiments, the device comprises a cannula assembly that includes the sealing element release means and a cannula, such as a hypodermic needle. The cannula may be fluidly connectable to the outlet by way of the sealing element release means when the outlet is open. The device may further comprise a cap for sealing a distal end of the needle or cannula. The cartridge may comprise a seal arrangement for sealing a proximal end of the sealing element release means in an enclosed chamber adjacent the sealing element, so that the sterility of the sealing element release means, the passage and the cannula can be preserved before use of the device.

In other embodiments, the device comprises an adaptor cap that includes the sealing element release means, a chamber that is fluidly connectable to the outlet by way of the sealing element release means when the outlet is open, and a further sealing element for releasably sealing a distal end of the chamber.

In either configuration, when a clamp arrangement is provided for attaching a component of the device, such as a mixing drive element or a delivery drive element, to the second container, the clamp arrangement may be arranged to apply a radial clamping force to the second container. For example, the clamp arrangement may comprise a clamping ring for applying the radial clamping force, and a clamping member for pressing the clamping ring into engagement with the second container. The clamping member may be in threaded engagement with the drive element. Similar clamp arrangements may be provided for attaching device components to the first container, where appropriate.

When relative movement between the first and second containers during the mixing stroke of the device causes movement of the mixing drive element or, when present, the delivery drive element from an initial position into an operating position, the mixing drive element or the delivery drive element may be partially or fully retracted in a housing part of the device, such as the cartridge holder, when in the initial position. Accordingly, the mixing drive element or the delivery drive element may emerge from the housing after the mixing stroke. When the mixing drive element or the delivery drive element is to be manually operated to perform the delivery stroke, the movement of the corresponding drive element from the initial position to the operating position during the mixing stroke provides the user with an indication that the delivery stroke is ready to be performed, and can prevent premature operation of the delivery stroke.

In other arrangements, an operating member, such as a trigger button, could be coupled to the movement of the second container in such a way that the operating member moves from an initial position to an operating position during the mixing stroke.

In a second aspect of the present invention, there is provided a cartridge for packaging medicament substances for use with a delivery device or an adaptor for a delivery device, comprising a first container having a first chamber for storage of a first substance and an outlet disposed at the distal end of the first chamber, a sealing element for closing the outlet, a second container arranged coaxially with respect to the first container and having a second chamber for storage of a second substance, valve means for closing a distal end of the second chamber, and stopper means for closing a proximal end of the second chamber. The stopper means is movable with respect to the second container, and the second container is at least partially received in the first container to close the proximal end of the first chamber when the valve means is closed.

The second container is movable in the proximal direction with respect to the first container to open the valve means and to displace the second substance into the first chamber through the valve means when the outlet is closed, thereby to cause mixing of the first and second substances. The second container is movable in the distal direction with respect to the first container to close the valve means and to displace the mixed first and second substances through the outlet when the outlet is open.

With this arrangement, the cartridge provides a simple packaging for a two-component medicament in which the first and second substances can be kept apart and in sterile conditions until required. The first and second substances can be mixed within the cartridge during a mixing stroke, in which the second container moves proximally with respect to the first container (or, equivalently, the first container moves distally with respect to the second container), and then delivered through the outlet in a delivery stroke, in which the second container moves distally with respect to the first container. Because the mixing and delivery strokes can be achieved by simple movements of the second container with respect to the first container that can be readily driven by suitable drive mechanisms, the cartridge can be used with a wide variety of medicament delivery devices.

Furthermore, because the valve means is able to open upon proximal movement of the second container with respect to the first container at the start of the mixing stroke, a separate initial step to open the valve means is not required, and the mixing stroke can be driven either by driving the stopper in the distal direction or by driving the second container in the proximal direction. Accordingly, the cartridge provides for two different operating configurations, and a greater degree of design flexibility is available when designing devices for use with the cartridge. Closure of the valve means during the delivery stroke can reduce the hydraulic length of the system and can increase the accuracy of the delivered volume.

The cartridge may comprise an inner closure member disposed at the distal end of the second container. Preferably, the inner closure member comprises the valve means. To minimise the component count and the number of materials in contact with the substances, the inner closure member may also provide a seal between the second container and the first container. To this end, the inner closure member may comprise one or more annular ridges for cooperation with an inner wall of the first container.

Similarly, the valve means may be formed integrally with the inner closure member.

The inner closure member may be elastomeric. For example, the inner closure member may be of a natural or synthetic rubber material. The inner closure member may be cap shaped, and the second container may comprise a collar for retaining the inner closure member. The inner closure member may be fitted over a neck part of the second container.

Preferably, the valve means comprises a one-way valve. In this way, the valve means can be arranged to open in conditions where the pressure in the second chamber is greater than the pressure in the first chamber and to close in conditions where the pressure in the second chamber is less than the pressure in the first chamber.

When the valve means comprises a one-way valve, any suitable one-way or check valve design can be employed. The valve may comprise two or more valve elements biased to seal against one another and to spread apart from one another in response to a pressure differential across the valve means. For example, the valve means may comprise a slit valve.

In a variation of the second aspect of the invention, closure of the valve means after the mixing stroke is optional. For example, in this case, the valve means may comprise a membrane that is arranged to split, detach, rupture or otherwise open at the start of the mixing stroke.

The sealing element keeps the outlet of the cartridge closed during the mixing stroke and allows the outlet to open during the delivery stroke. To this end, the cartridge may be cooperable with a delivery device or adaptor device to open the outlet after the mixing stroke and before the delivery stroke.

For example, the sealing element may comprise a pierceable septum. The cartridge may be cooperable with the device in such a way that the septum is pierced by a piercing member of the device to open the outlet after the mixing stroke and before the delivery stroke.

The cartridge may comprise an outer closure member disposed at the distal end of the first container. The outer closure member may comprise the sealing element. For example, the outer closure member may include a pierceable septum. In an embodiment, the outer closure member comprises a disc disposed at the distal end of the outer container. The outer closure member may be elastomeric, and may be formed from a natural or synthetic rubber material.

A coupling element may be provided for coupling the cartridge to the delivery device or adaptor device. In this way, a common coupling arrangement can be used to allow the cartridge to be used with multiple different types of device. The coupling element is preferably disposed at the distal end of the first container. In an embodiment, the first container comprises a collar, and the coupling element clips to the collar. The collar is preferably disposed on a reduced-diameter neck of the first container.

The coupling element may comprise the sealing element, or may retain the sealing element. When an outer closure member is present, the coupling element may retain the outer closure member. In an alternative arrangement, the outer closure member is retained by the first container, and the coupling element is retained by the outer closure member.

The coupling element may be arranged to couple the cartridge to the delivery device or adaptor device in a first attachment position in which the outlet is closed and a second attachment position in which the sealing element is released by a sealing element release means of the delivery device or adaptor to open the outlet. In this way, the cartridge and device can be supplied to a user when arranged in the first attachment position. To prepare the device for use, the substances in the cartridge can be mixed, and then the cartridge and device can be switched into the second attachment position to open the outlet before the delivery stroke.

When the sealing element comprises a pierceable septum, the sealing element release means may comprise a piercing member arranged to pierce the septum when the cartridge is moved from the first attachment position to the second attachment position. For example, the piercing member may be an internal needle or the proximal part of a double-ended needle.

The coupling element may be arranged for cooperation with an engagement part of the delivery device or adaptor device to clip the cartridge to the device upon insertion of the cartridge. To this end, the coupling element may comprise an engagement formation for engagement with an engagement part of the device.

The cartridge may comprise a seal arrangement for sealing a proximal end of a sealing element release member of the delivery device or the adaptor device in an enclosed chamber adjacent to the sealing element before release of the sealing element to open the outlet. In this way, the sterility of the sealing element release member can be preserved when the cartridge is coupled to the device and before the sealing element is released, allowing the cartridge and device to be supplied in a pre-assembled configuration. For example, when the cartridge can be coupled to the device in a first attachment position in which the outlet is closed and a second attachment position in which the sealing element is released by the sealing element release member, the cartridge and device can be supplied in the first attachment position with the proximal end of the release member sealed in the enclosed chamber formed by the seal arrangement.

The seal arrangement may be disposed distally with respect to the sealing element. The seal arrangement may be arranged to form a seal around the release member when the cartridge is coupled to the delivery device or adaptor. In an embodiment, the seal arrangement comprises a bore for receiving the release member. When an outer closure member is provided, the outer closure member may comprise the bore. When a coupling element is provided, the coupling element may comprise the bore. In either case, the bore may include a reduced-diameter region for forming the seal around the release member. A sealing ring, such as an O-ring, may be provided for forming the seal.

The first and second containers are preferably generally tubular. For example, the first and/or second container may comprise a container body that is tubular over at least a major portion of the body. In an initial state of the cartridge, the second container may protrude proximally from the first container. The second container is preferably cooperable with a clamping arrangement of a delivery device or adaptor device.

In a third aspect of the invention, a device comprising a cartridge holder for receiving a cartridge according to the second aspect of the invention is provided. The device is operable to cause relative movement between the first container and the second container when the outlet is closed to cause mixing of the first and second substances in a mixing stroke of the device. The device may be in accordance with the first aspect of the invention.

In a fourth aspect the invention provides, in combination, a device according to the first or third aspects of the invention and a cartridge according to the second aspect of the invention.

In a fifth aspect, the invention extends to a method of assembling a medicament delivery device or an adaptor device for a medicament delivery device. The method comprises inserting, into a cartridge holder of the device, a medicament cartridge comprising a first container having a first chamber for storage of a first substance, an outlet disposed at the distal end of the first chamber, closure means for closing the outlet, a second container at least partially received in the first container and having a second chamber for storage of a second substance, valve means for closing a distal end of the second chamber and a proximal end of the first chamber, and stopper means for closing a proximal end of the second chamber, the stopper means being movable with respect to the second container; and securing a drive element of the device to the first container or the second container of the cartridge. It will be appreciated that the drive element could be secured to the first or second container of the cartridge either before or after the cartridge is inserted into the cartridge holder.

The method may comprise applying a clamping force to a body of the first or second container to secure the drive element to the container. For example, the method may comprise applying the clamping force to an outside wall of the container body, or to an inside wall of the container body. The method may comprise turning a clamping member with respect to the drive element to apply the clamping force to the container body.

The method may further comprise latching the drive element in an initial position with respect to the holder. For example, the drive element may be biased for movement by a drive spring, and the method may comprise compressing the drive spring before latching the drive element in the initial position.

In a further aspect of the invention, there is provided a cartridge for packaging medicament substances, comprising a first container having a first chamber for storage of a first substance and an outlet disposed at the distal end of the first chamber, a sealing element for closing the outlet, a second container arranged coaxially with respect to the first container and having a second chamber for storage of a second substance, valve means for closing a distal end of the second chamber, stopper means for closing a proximal end of the second chamber, the stopper means being movable with respect to the second container, and a coupling element disposed at a distal end of the first container for coupling the cartridge to a delivery device or to an adaptor for a delivery device. The second container is at least partially received in the first container to close the proximal end of the first chamber when the valve means is closed. The second container is movable in the proximal direction with respect to the first container to displace the second substance into the first chamber through the valve means when the outlet is closed, thereby to cause mixing of the first and second substances. The second container is movable in the distal direction with respect to the first container to displace the mixed first and second substances through the outlet when the outlet is open.

In another aspect of the invention, there is provided a cartridge for packaging medicament substances, comprising a first container having a first chamber for storage of a first substance and an outlet disposed at the distal end of the first chamber, a sealing element for closing the outlet, a second container arranged coaxially with respect to the first container and having a second chamber for storage of a second substance, a closure means for closing a distal end of the second chamber, and stopper means for closing a proximal end of the second chamber, the stopper means being movable with respect to the second container. The second container is at least partially received in the first container to close the proximal end of the first chamber when the closure means is closed. The second container is movable in the proximal direction with respect to the first container to open the closure means and to displace the second substance into the first chamber when the outlet is closed, thereby to cause mixing of the first and second substances. The second container is movable in the distal direction with respect to the first container to displace the mixed first and second substances through the outlet when the outlet is open.

In a still further aspect of the invention, there is provided a cartridge for packaging medicament substances, comprising a first container having a first chamber for storage of a first substance and an outlet disposed at the distal end of the first chamber, a second container arranged coaxially with respect to the first container and having a second chamber for storage of a second substance, valve means for closing a distal end of the second chamber, stopper means for closing a proximal end of the second chamber, the stopper means being movable with respect to the second container, and a coupling element disposed at a distal end of the first container for attaching the cartridge to a delivery device or to an adaptor for a delivery device in a first position in which the outlet is closed and in a second position in which the outlet is open. The second container is at least partially received in the first container to close the proximal end of the first chamber when the valve means is closed. The second container is movable in the proximal direction with respect to the first container to displace the second substance into the first chamber through the valve means when the outlet is closed, thereby to cause mixing of the first and second substances. The second container is movable in the distal direction with respect to the first container to displace the mixed first and second substances through the outlet when the outlet is open.

In another aspect of the invention, a device for mixing first and second substances in a cartridge as described with reference to any of the above aspects of the invention is provided. The device comprises a cartridge holder for receiving the cartridge, a drive element, and an operating mechanism for driving movement of the drive element with respect to the cartridge holder upon activation of the operating mechanism, thereby to cause movement of the second container in the proximal direction to open the valve means and to displace the second substance into the first chamber through the valve means when the outlet is closed to cause mixing of the first and second substances in a mixing stroke of the device.

An addition aspect of this invention is directed to one or more of the medicaments, including one or more pharmaceutical compositions, as described above for subcutaneous injection or infusion, disposed within the medicament delivery devices described herein for the delivery of the medicament. Additionally, this invention contemplates methods of administering one or more of the medicaments, including pharmaceutical compositions, to patients with conditions susceptible to treatment with the medicaments, as well as methods of treating those conditions, by delivering the appropriate medicament using the delivery devices described herein.

Preferred and/or optional features of each aspect of the invention may be used, alone or in appropriate combination, with the other aspects of the invention also.

Although the present invention is particularly useful for packaging a reconstitutable medicament, the invention can be equally applied to other applications in which two or more starting substances are to be mixed. It will be understood that, in the context of this specification, the term "mixture" is used to refer to any chemical or physical combination of two or more starting substances, and references to "mixing", "mixed" and related terms should be construed accordingly. Thus "mixing" should be taken to include the formation of a solution, suspension, emulsion, colloid, gel, sol, foam, and so on. The term "mixing" also includes the bringing together of two or more reactants that react together upon mixing to form a new chemical compound.

Embodiments of the present invention will now be described, by way of example only, with reference to the accompanying drawings, in which like reference numerals are used for like features, and in which.

Figure 1:
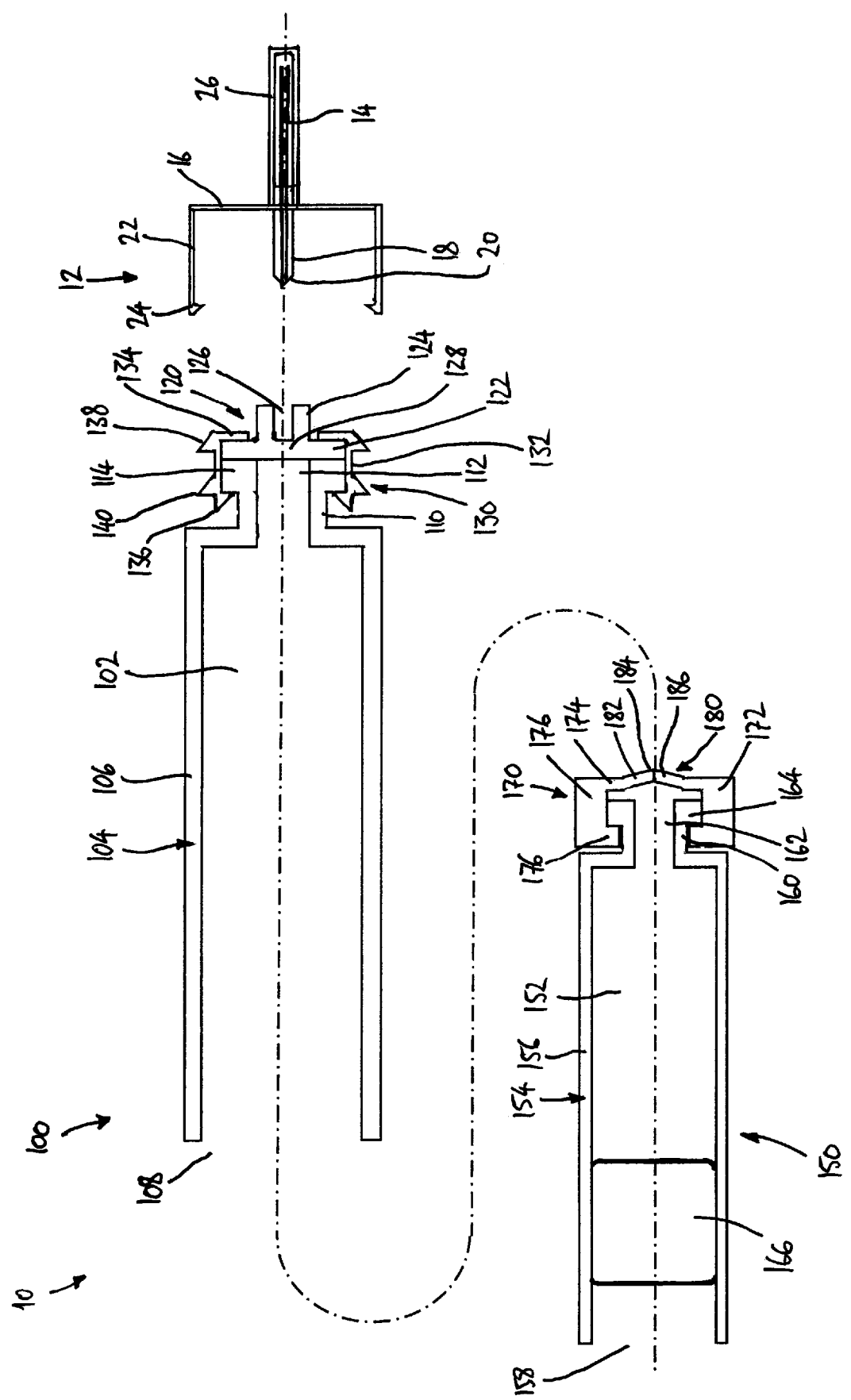
FIG. 1 shows schematic cross-sectional views of components of a medicament cartridge together with a needle assembly of a delivery device.

FIG. 1 shows, in schematic form, components of a medicament package or cartridge 10 according to an embodiment of the present invention, together with a needle assembly 12 of a delivery device that is suitable for use with the cartridge 10.

The cartridge 10 is arranged to contain two medicament substances in separate respective chambers until the medicament is to be administered. The cartridge 10 is operable to first mix the medicament substances together within the cartridge 10, and then to express the mixture from the cartridge 10 for administration to a patient. To this end, the cartridge 10 comprises a first or outer container 100 that includes a first chamber 102 for receiving a first medicament substance, and a second or inner container 150 that includes a second chamber 152 for receiving a second medicament substance. FIG. 1 shows the first container 100 and the second container 150 separately, but in use the second container 150 is partly housed in the first container 100.

The first container 100 comprises a container body 104 that defines the first chamber 102. The first container body 104 includes a tubular major part 106 with an open proximal end 108, and a distal part comprising a reduced diameter neck 110 that provides an outlet 112 of the first chamber. An annular flange or collar 114 extends around the neck 110 adjacent to its distal end. In this example, the tubular major part 106, neck 110 and collar 114 of the body 102 are integrally formed from glass or another suitable material (such as a biocompatible and pharmacologically inert plastics material).

The outlet 112 is closed by a first or outer closure member 120, formed for example from an elastomeric material (such as a halobutyl or other rubber material). The closure member 120 comprises a sealing disc 122 having a flat proximal face that forms a seal against the distal end of the neck 110. A tubular throat 124 extends distally from the sealing disc 122 to define a bore 126. The distal end of the bore 126 is open, whilst the proximal end of the bore 126 is closed by the sealing disc 122. In this way, the part of the sealing disc 122 that closes the bore 126 defines a sealing element for the distal end of the first chamber in the form of a pierceable septum 128.

The closure member 120 is retained in place on the distal end of the first container body 102 by a coupling element 130. The coupling element 130 may be formed from a rigid plastics material, such as polyoxymethylene (POM) or polypropylene (PP). The coupling element 130 comprises an annular body or ring part 132 having an inwardly-directed flange 134 at its distal end for retaining the closure member 120, and a plurality of inwardly-facing clip formations 136 at its proximal end. The clip formations 136 are shaped to engage with the proximal side of the collar 114 of the first container body 102 when the closure member 120 is pressed onto the neck 110 during assembly, so as to clamp the sealing disc 122 of the closure member 120 to the distal end of the first container body 102.

The outer surface of the annular body 132 carries a first or distal engagement formation 138 and a second or proximal engagement formation 140. In this example, each engagement formation 138, 140 comprises an annular rib or projection with a ramped distal face and a perpendicular proximal face. The first engagement formation 138 is disposed adjacent to the distal end of the coupling element 130, and the second engagement formation 140 is proximally spaced from the first engagement formation 138.

As will be explained in more detail below, the first and second engagement formations 138, 140 are arranged to engage with the needle assembly 12 to clip the cartridge 10 to the needle assembly 12 in one of two insertion or attachment positions.

The needle assembly 12 comprises a hypodermic needle 14 that is mounted to a needle holder 16. The needle holder 16 includes a generally tubular, proximally-extending piercing member 18. The lumen of the needle 14 is in fluid communication with the bore of the piercing member 18. The proximal tip 20 of the piercing member 18 is sharpened to enable the piercing member 18 to puncture the septum 128 in use. A plurality of arms 22 extend proximally from the needle holder 16. The proximal end of each arm 22 is provided with a clip 24 that is arranged to cooperate with each of the engagement formations 138, 140 of the coupling element 130, so that the arms 22 and the associated clips 24 define a cartridge connector of the needle assembly 12. A removable needle cap 26 is fitted over the needle 14 to maintain sterility of the needle 14 prior to use.

The second container 150 comprises a container body 154 that defines the second chamber 152. The second container body 154 is similar in shape and construction to the first container body 104, and thus comprises a tubular major part 156 having a proximal end 158, a neck 160 providing an outlet 162 of the second chamber 152, and a collar 164 that extends around the neck 160 at its distal end. The outer diameter of the tubular part 156 of the second container body 154 is less than the inner diameter of the corresponding tubular part 106 of the first container body 102, so that the second container 100 can be received in the tubular part 106 of the first container body 102 with a clearance between the respective tubular parts 106, 156.

An elastomeric bung or stopper 166 is received in the tubular part 156 of the second container body 154 to close the proximal end of the second chamber 152. The stopper 166 is sized to form a seal against the internal wall of the tubular part 156 of the second container body 154, and is slidable with respect to the second container body 154 in use.

The distal end of the second container body 154 is closed by a second or inner closure member 170 in the form of a cap 172 that fits over the collar 164 of the second container body 154. The cap 172 comprises a distal face 174 and an annular ring part 176 that extends proximally from the distal face 174 to receive the neck 164 of the second container body 154. An inwardly-directed flange 176 is disposed at the proximal end of the cap 172 to engage around the neck 160 on the proximal side of the collar 164 to secure the cap 172 to the second container body 154. The annular ring part 176 has an outer diameter that is larger than the outer diameter of the tubular major part 156 of the second container body 154, and is sized so that a seal is formed between the cap 172 and the inner wall of the tubular major part 106 of the first container body 104 when the second container 200 is received in the proximal end 108 of the first container 100.

The cap 172 is formed from an elastomeric material, such as a halobutyl or other rubber material. The inner dimensions of the cap 172 are such that the cap 172 is slightly deformed when fitted over the collar 164 of the neck 160 of the second container body 154. In this way, a seal is formed between the cap 172 and the outer surfaces of the neck 160 and the collar 164.

The distal face 174 of the cap 172 is formed to provide a one-way slit valve 180 for closing the distal end of the second chamber 152. To this end, the distal face 174 comprises a generally wedge-shaped region 182 that faces away from the second chamber 152 (i.e. the ridge of the wedge-shaped region 182 extends from the distal side of the cap 172), and a slit 184 extends through the cap 172 along the ridge to divide the wedge-shaped region 182 into a pair of valve members 186.

The valve members 186 are biased towards one another so that, when fluid pressures on each side of the slit valve 180 are equal, the valve members 186 seal against one another to close the slit 184. When the pressure on the proximal side of the slit valve 180 is sufficiently greater than the pressure on the distal side, the bias of the valve members 186 can be overcome to cause the valve members 186 to part to allow fluid flow through the slit valve 180 in the distal direction. However, when the pressure on the distal side of the slit valve 180 exceeds the pressure on the proximal side, the valve members 186 are urged towards one another to close the slit 184. In this way, fluid flow through the slit valve 180 is only possible in the distal direction.

FIGS. 2(a) to 2(e) show the assembled cartridge 10 with the needle assembly 12 attached, in a sequence of operational steps in use of the cartridge 10.

FIG. 2(a) shows the cartridge 10 in a starting state, as it would be supplied by a manufacturer. The first chamber 102 contains the first medicament substance, which may for example be a powder or granulated solid. The second container 150 is received in the proximal end 108 of the first container 100, so that the first chamber 102 is closed at its proximal end by the second closure member 170 of the second container 150. The outlet 112 at the distal end of the first chamber 102 is closed by the septum 128 of the closure member 120. The length of the second container 150 is such that a proximal end part of the second container body 154 extends out of the proximal end 108 of the first container 100.

The second chamber 152, in the second container, contains the second medicament substance, which is typically a liquid. The second chamber 152 is closed at its proximal end by the stopper 166 and at its distal end by the second closure member 170. In this starting state, the slit valve 180 is closed to seal the distal end of the second chamber 152 and the proximal end of the first chamber 102, so that the first and second medicament substances are kept apart until mixing is required.

The needle assembly 12 is mounted to the cartridge 10 in a first attachment position, with the clips 24 engaged with the first engagement formations 138 of the coupling element 130. In this first attachment position, the piercing member 18 is received in the bore of the throat 124, but the piercing member 18 does not pierce the septum 128.

The walls of the throat 124 are shaped to form a seal around the piercing member 18. Thus, when in the first attachment position, the proximal end of the piercing member is enclosed in a closed chamber adjacent to and on a distal side of the septum 128. Together with the needle cap 26, this seal arrangement ensures that the sterility of the needle 14 is preserved.

In a first phase of operation, mixing of the substances is driven by movement of the second container 150 in the proximal direction with respect to the first container 100, as shown in FIG. 2(b). Because the outlet 112 of the first chamber 102 is sealed by the septum 128, the total volume of the first and second chambers 102, 152 must be conserved. Thus, as the second container 150 moves proximally with respect to the first container 100 in a mixing stroke, the volume of the first chamber 102 increases and the slit valve 180 opens to allow the second medicament substance in the second chamber 152 to flow into the first chamber 102 to mix with the first medicament substance. The stopper 166 moves distally with respect to the second container 150 as the volume of the second chamber 152 decreases.

FIG. 2(c) shows the arrangement at the end of the mixing stroke of the second container 150. At this point, the pressure on each side of the slit valve 180 equalises, so that the slit valve 180 closes once more.

Having mixed the first and second medicament substances, the mixed medicament can now be delivered from the cartridge 10. To allow delivery of the medicament, the cartridge 10 is moved distally with respect to the needle assembly 12 into a second insertion or attachment position, as shown in FIG. 2(d). In the second attachment position, the clips 24 of the needle assembly 12 engage with the second engagement formation 140 of the coupling element 130, and the piercing member 18 pierces the septum 128. The outlet 112 at the distal end of the first chamber 102 is now open and in fluid communication with the needle 14, by way of the piercing member 18. The needle cap 26 is removed to expose the needle 14.

To express the medicament from the needle 14, the second container 150 is moved in the distal direction with respect to the first container 100 in a medicament delivery stroke that occurs during a second phase of operation of the cartridge 10. As the second container 150 moves in the distal direction, the slit valve 180 remains closed, so that the second closure member 170 acts as a piston that reduces the volume of the first chamber 102. The mixed medicament is thus forced out of the first chamber 102 through the needle 14. FIG. 2(e) shows the arrangement towards the end of the medicament delivery stroke, when the mixed medicament has been delivered through the needle 14.

The components of the cartridge 10 can be supplied as a kit of parts to allow the cartridge 10 to be loaded with the first and second medicament substances by a medicament manufacturer. Although several different procedures can be used to load the cartridge 10, in one example the stopper 166 is placed in position in the second container body 154, the second chamber 152 is filled with the second medicament substance from the distal end of the second container 150, and then the second closure member 170 is fitted to seal the second chamber 152. The second container 150 is then placed in position in the first container body 104 to close the proximal end of the first chamber 102, and the first chamber 102 is then filled with the first medicament substance. Finally, the first closure member 120 is placed on the distal end of the first container body 104 and secured by clipping the coupling element 130 into place. With this sequence of steps, it is possible to substantially exclude air from the first and/or the second chamber 102, 152 if required.

Figure 2:
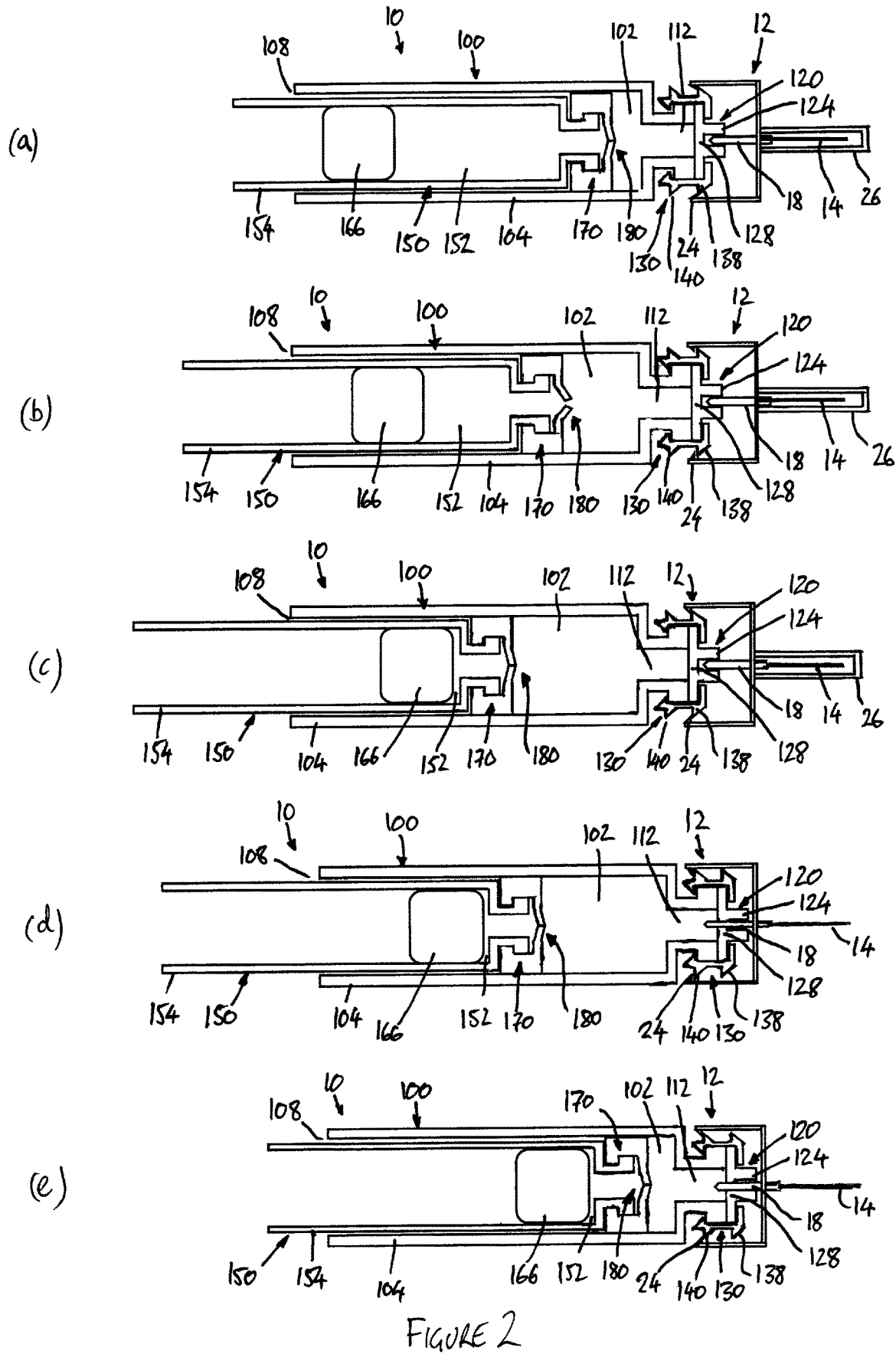
FIG. 2 shows schematic cross-sectional views of a sequence of steps during operation of the medicament cartridge of FIG. 1.

In practice, two different methods can be used to operate the cartridge 10 as shown in FIG. 2. In a first method, the first container body 104 and second container body 154 are moved relative to one another by a suitable mechanism of a delivery device, and the stopper 166 is free to move in the second cartridge body 150 to accommodate the exchange in volume between the first and second chambers 102, 152 during the mixing stroke. In this case, during the mixing stroke, the second container body 154 is moved proximally with respect to the first container body 104 (or, equivalently, the first container body 104 is moved distally with respect to the second container body 154) and the pressure in the first chamber 102 is reduced. The flow of the second medicament substance into the first chamber 102 through the slit valve 180 is driven by this "negative" pressure in the first chamber 102. Subsequently, the second container body 154 is moved distally to expel the medicament.

In a second method, a drive mechanism of a delivery device applies a drive force directly to the stopper 166 to drive the stopper distally with respect to the first container body 104. In this case the second container body 154 is free to move to accommodate the exchange in volume between the first and second chambers 102, 152 during the mixing stroke. Thus, in the mixing stoke, the force applied to the stopper 166 increases the fluid pressure in both the first and second chambers 102, 152, with the result that the second container body 154 moves proximally with respect to the first container body 104. In this case, the flow of the second medicament substance into the first chamber 102 through the slit valve 180 is driven by the "positive" pressure in the second chamber 152. The second container body 154 can then be moved in the distal direction to expel the medicament through the needle 14.

It will be appreciated from FIG. 2 that the relative movement of the first and second containers 100, 150 and the stopper 166, and the operation of the slit valve 180, is the same regardless of which of these methods is used. Advantageously, therefore, a cartridge 10 of the type shown in FIGS. 1 and 2 can be used in different delivery devices that have substantially different operating mechanisms. In this way, a reconstitutable medicament can be supplied in a single package type for use with multiple delivery devices.

Figure 3:
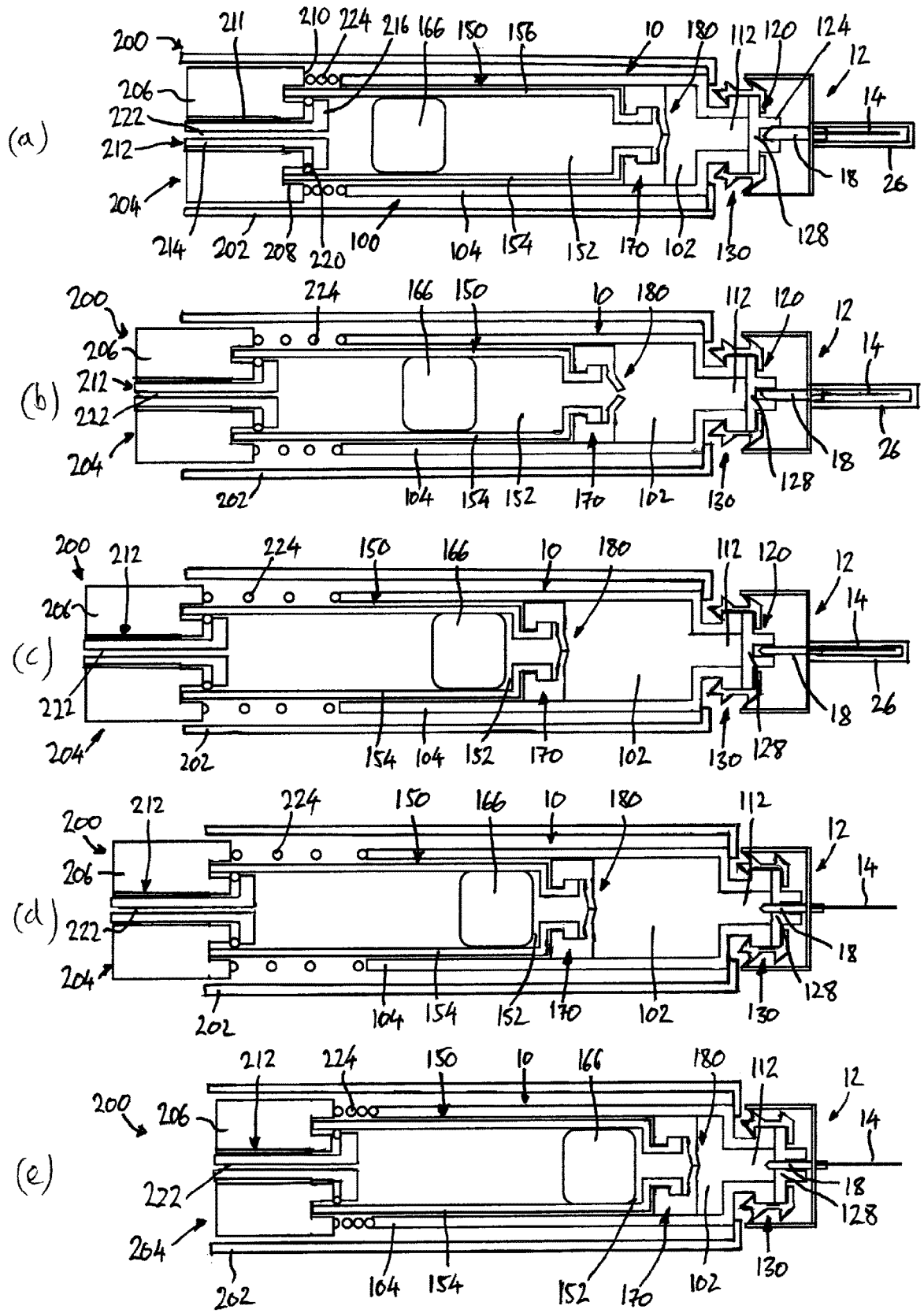
FIG. 3 shows schematic cross-sectional views of a sequence of steps during operation of the medicament cartridge of FIG. 1 when in use with a delivery device of a first type.

FIG. 3 illustrates, schematically, the cartridge 10 in use with a medicament dosing or delivery device 200 having a drive mechanism that operates using the first method, in which the mixing of the substances is driven by a reduction in the pressure in the first chamber 102. In this case, the second container body 154 is driven for movement with respect to the first container body 104.

Referring to FIG. 3(a), the delivery device 200 comprises a holder 202 for receiving and retaining the cartridge 10, and a drive element 204 that is moveable with respect to the holder 202. The holder 202 engages with the cartridge 10 in such a way that the first container body 104 is fixed in position with respect to the holder 202. The drive element 204 is coupled for joint axial movement with the second container body 154.

The drive element 204 comprises a generally cylindrical button 206 disposed proximally with respect to the second container body 154, with a proximal end part of the second container body 154 received in an annular recess 208 formed in the distal face 210 of the button 206.

A clamping arrangement is provided to secure the drive element 204 to the second container body 154. A threaded bore 211 extends axially through the button 206 to receive a clamping rod 212 of the drive element 204. A shaft part 214 of the clamping rod 212 is threaded for engagement with the bore 211, and a disc-shaped head part 216 is disposed at the distal end of the shaft part 214, with the head part 216 received in the proximal end of the second container body 154.

A clamping ring 220, comprising an elastomeric O-ring, is retained in a space between the head part 216 of the clamping rod 212 and the distal face 210 of the button 206. The clamping ring 220 is sized to conform to the inner diameter of the tubular major part 156 of the second container body 154. During assembly of the device 200, with the clamping ring 220 disposed in the second container body 154, the clamping rod 212 can be turned to decrease the space between the head part 216 of the clamping rod 212 and the distal face 210 of the button 206 to squeeze the clamping ring 220 against the inner wall of the second container body 154, thereby applying a radial clamping force to the second container body 154 that locks the second container body 154 to the drive element 204.

A vent passage or bore 222 extends axially through the clamping rod 212, to provide a venting means that admits air into the space between the stopper 166 and the head part 216 of the clamping rod 212. In this way, the stopper 166 remains free for movement with respect to the second container body 154 during operation of the device 200.

The drive element 204 is biased in the distal direction with respect to the first container 100 by means of a drive spring 224. In this example, a proximal end of the drive spring 224 acts on the distal face 210 of the button 206, and a distal end of the drive spring 224 acts on the proximal end of the first container body 104, although it will be appreciated that other arrangements are possible (for example, the distal end of the spring 224 could instead act on the cartridge holder 202 or another part of the device 200).

In an initial state of the device, shown in FIG. 3(a), the cartridge 10 is in its starting state, corresponding to FIG. 2(a), in which the first and second medicament substances are contained separately in the respective first and second chambers 102, 152. The drive element 204 is latched or otherwise held in an initial position with respect to the cartridge holder 202 with a suitable latch mechanism (not shown). When held in this initial position, the drive element 204 applies no axial force to the second container body 154. The needle assembly 12 is attached to the coupling element 130 in the first attachment position, in which the septum 128 of the closure member 120 is not pierced by the piercing member 18 of the needle assembly 12.

To mix the medicament substances, the latch mechanism is released to allow the drive element 204 to move with respect to the cartridge holder 202 and the first container body 104. In particular, the drive spring 224 urges the button 206 in the proximal direction, which in turn causes the second container body 154 to be pulled proximally with respect to the first container body 104, as shown in FIG. 3(b). The resulting pressure drop in the first chamber 102 causes the slit valve 180 to open, and the second medicament substance flows from the second chamber 152 into the first chamber 102 to mix with the first medicament substance. The stopper 166 moves distally with respect to the second container body 154, with air being admitted to the second container body 154 on the proximal side of the stopper 166 through the vent passage 222 in the clamping rod 212.

At the end of the mixing stroke of the second container 150, the slit valve closes 180, as shown in FIG. 3(c). The first chamber 102 now contains the mixture of the first and second medicament substances.

To ready the device 200 for delivery of the mixed medicament, the needle assembly 12 is moved into the second attachment position so that the piercing member 18 pierces the septum 128 and the needle cap 26 is removed, as shown in FIG. 3(d).

The mixed medicament can then be expressed through the needle 14 by pushing the button 206 in the distal direction, against the bias of the drive spring 224. This causes the second container 150 to move distally with respect to the first container 100 to reduce the volume of the first chamber 102 and release the medicament, as shown in FIG. 3(e).

Figure 4:
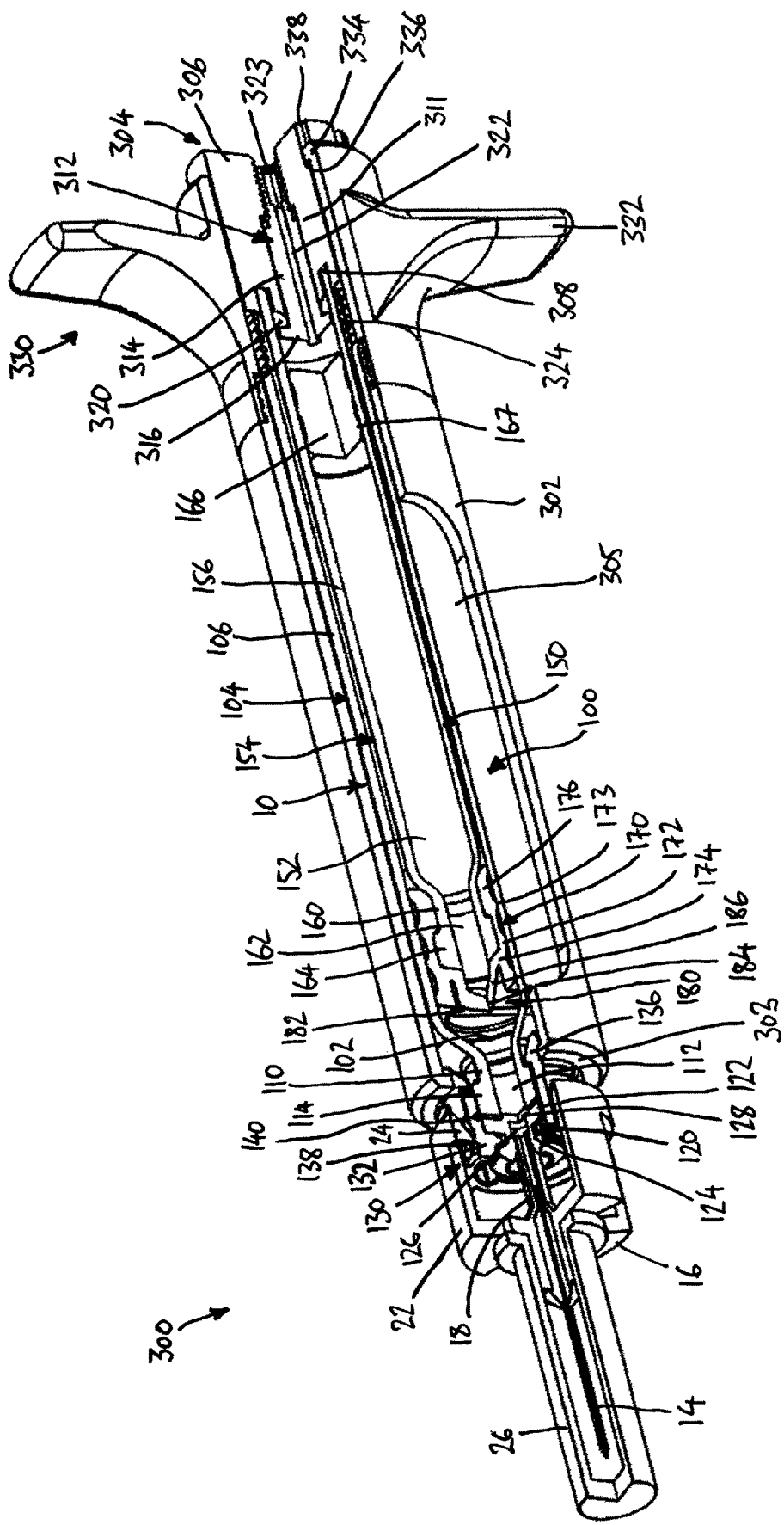
FIG. 4 is a cut-away perspective view of an embodiment of a delivery device of the first type in use with a medicament cartridge of the type shown in FIG. 1.

FIG. 4 shows an example of a device that operates on the principle described with reference to FIG. 3. In this example, the device 300 is a manually-operated, disposable syringe.

The device 300 includes a needle assembly 12 and houses a cartridge 10, and both the needle assembly 12 and the cartridge 10 are of the type described above with reference to FIGS. 1 and 2. Thus, in FIG. 4, like reference numerals are used to denote functionally equivalent features to those described with reference to FIGS. 1 and 2, and only the differences will be described below.

First, in the cartridge 10 shown in FIG. 4, the stopper 166 is provided with a plurality of annular ridges 167 on its outer surface. As is known in the art, these ridges 167 help to ensure that a seal is formed between the stopper 166 and the inner wall of the second container body 154, whilst allowing the stopper 166 to slide smoothly in the second container body 154 when required. A plurality of annular ridges 173 are also formed on the outer surface of the cap 172 of the second closure member 170, for the same reason.

Furthermore, in the cartridge 10 shown in FIG. 4, the throat 124 of the first closure member 120 is mushroom-shaped, and the walls of the bore 126 of the throat 124 are shaped so that the bore 126 has a narrowed region. In this way, sealing between the piercing member 18 of the needle assembly 12 and the first closure member 120 is improved.

The device 300 of FIG. 4 is similar to that described above with reference to FIG. 3. The device 300 thus comprises a cartridge holder 302, which in this case is formed with a retaining ring 303 at its distal end. The retaining ring 303 engages with the coupling element 130 of the cartridge 10 to apply an inwardly-directed retaining force to the coupling element 130 that helps to keep the clips 136 of the coupling element 130 engaged behind the collar 114 of the first container body 104. Engagement of the retaining ring 303 with the coupling element 130 also serves to prevent movement of the cartridge 10 relative to the cartridge holder 302.

The cartridge holder 302 further includes a window 305 that allows the cartridge 10 to be viewed from outside the device. A proximal end fitting 330, having a pair of finger tabs 332, is in threaded engagement with the proximal end of the cartridge holder 302.

In common with the FIG. 3 device, in the FIG. 4 device the drive element 304 comprises a button 306 with a bore 311 for receiving the clamping rod 312. In this example, only a proximal end region of the bore 311 and the shaft 314 of the clamping rod 312 are threaded. A proximal end part 323 of the vent passage 322 through the clamping rod 312 is enlarged and shaped to accept a tool for turning the clamping rod 312 during assembly of the device, to press the clamping ring 320 into engagement with the second container body 154 after the second container body 154 has been located in the annular recess 308. The proximal face of the head part 216 is frustoconically shaped to press the clamping ring 320 radially against the inner wall of the second container body 154.

The drive element 304 is latched in its initial position, with the drive spring 324 in its compressed state, by engagement of an inwardly-projecting pin or key 334 with a shoulder 336 formed on the button 306. The key 334 is disposed on the end fitting 330, and the shoulder 336 is formed at the end of a first distally-extending portion 338 of a track or keyway 340 provided in the cylindrical outer face of the button 306.

Turning to FIG. 5(a), the drive element 304 can be released for movement in the proximal direction under the influence of the drive spring 324 by turning the button 306 with respect to the end fitting 330. The keyway includes a circumferentially-extending portion 340 to accommodate the key 334 during the turning movement. The circumferentially-extending portion 340 of the keyway opens into a second distally-extending portion 342, which is longer in the distal direction than the first distally-extending portion 338. Accordingly, when the key 334 is brought into register with the second distally-extending portion 340 of the keyway, as shown in FIG. 5(b), the button 306 becomes free to move in the proximal direction, allowing the drive element 304 to drive the mixing stroke of the second container 150.

FIG. 5(c) shows the device 300 after proximal movement of the drive element 304, at the end of the mixing stroke, and when the needle assembly 12 has been moved into the second attachment position with respect to the cartridge 10. The needle cap 26 has also been removed, so that the device 300 is now ready for injection of the mixed medicament.

To perform the injection, the button 306 can be moved in the distal direction with respect to the cartridge holder 302. Conveniently, the finger tabs 332 allow the device 300 to be held by a user between two fingers while the button 306 is depressed by the user's thumb. In this example, therefore, the delivery stroke of the second container 150 is driven manually by the user. FIG. 5(d) shows the device 300 at the end of the delivery stroke.

Figure 5:
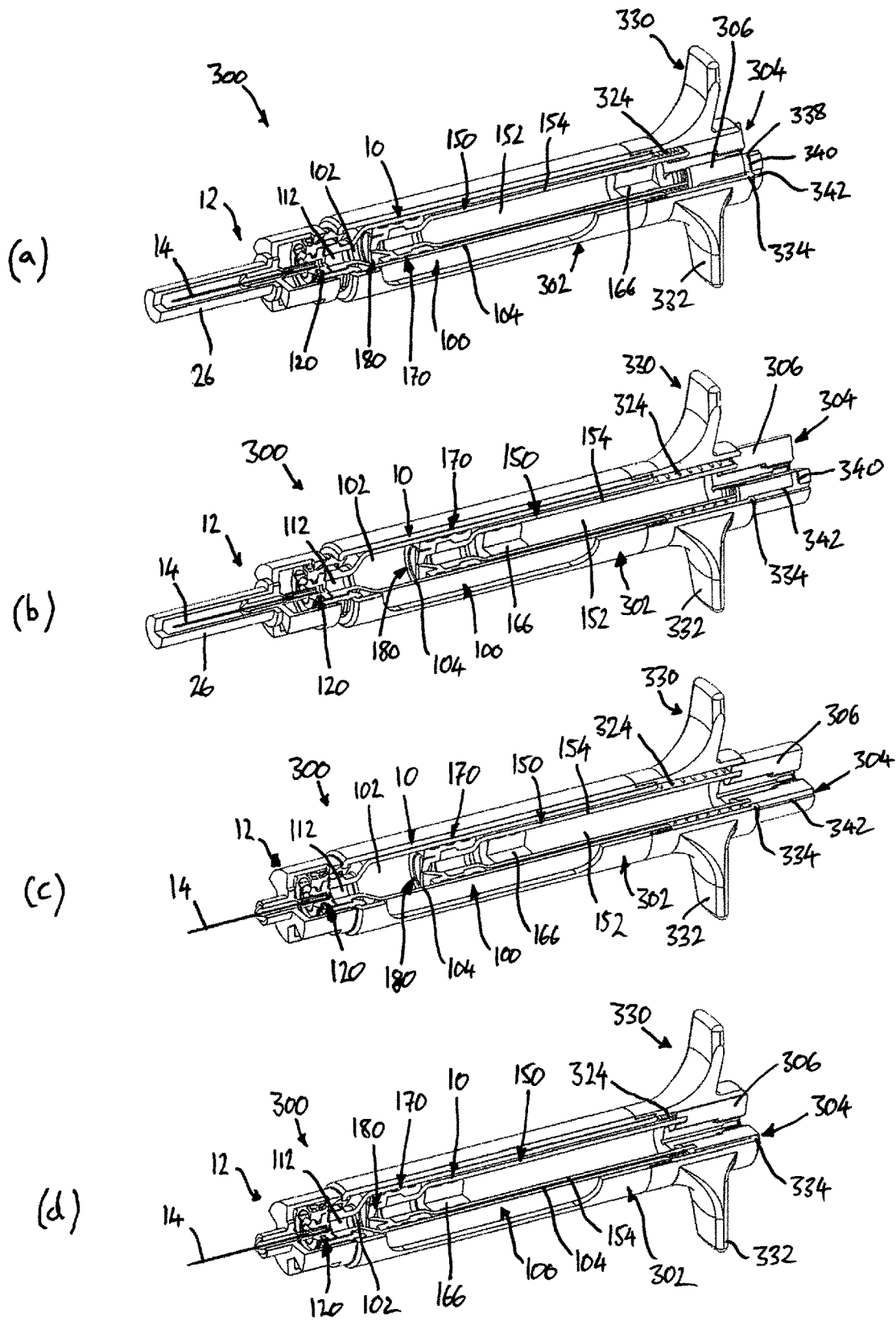
FIG. 5 shows cut-away perspective views of a sequence of steps during operation of the delivery device of FIG. 4.

In a variant of the device shown in FIGS. 4 and 5, the end fitting 330 is turnable with respect to the cartridge holder 302 about the axis of the device. In this case, the drive element 304 can be released by turning the end fitting 330 with respect to the holder 302 to move the key 334 into the second distally-extending portion 342 of the keyway, thereby to unlatch the drive element 304.

Figure 6:
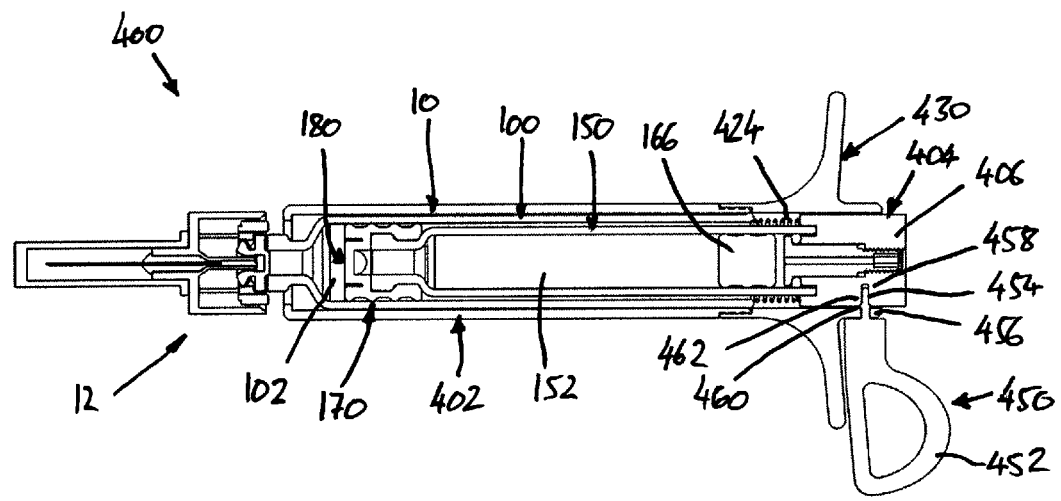
FIG. 6 shows cross-sectional views of a further embodiment of a delivery device of the first type in use with a medicament cartridge of the type shown in FIG. 1.
Figure 6:
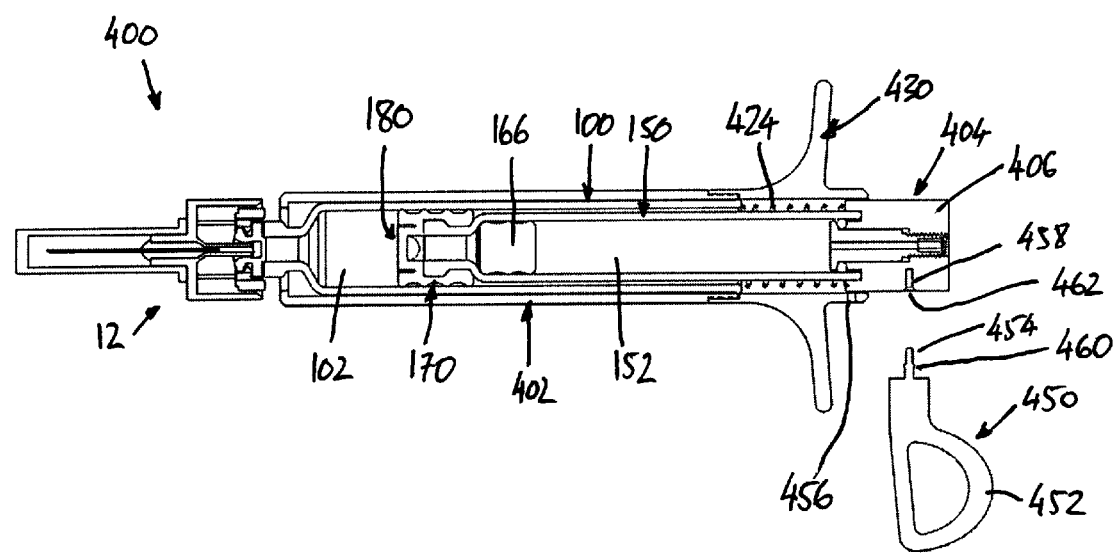

FIG. 6 shows another example of a device that operates on the principle described with reference to FIG. 3, again in the form of a manually-operated, disposable syringe.

The device 400 of FIG. 6 differs from the device 300 of FIGS. 4 and 5 only in the latch arrangement used to latch the drive element 404 in its initial position, and so only this difference will be described in detail.

Instead of a key and keyway arrangement, the device 400 of FIG. 6 is provided with a user-removable tab 450. The tab 450 includes a handle part in the form of a ring pull 452, and an elongate pin 454. As shown in FIG. 6(a), in the initial state of the device 400, the pin 454 of the tab 450 extends through an aperture 456 in the end fitting 430 and into a radially-disposed bore 458 of the button 406 of the drive element 404.

An annular ridge or detent 460 disposed on the pin 454 engages with a corresponding recess 462 at the outer end of the bore 458. The diameter of the detent 460 is slightly larger than the aperture 456, so that a threshold force must be applied pull the detent 460 through the aperture 456 to release the pin 454.

The pin 454 therefore holds the button 406 in its initial position, with the drive spring 424 compressed. The pin 454 can be removed by pulling the tab 450, which releases the drive element 404 for proximal movement with respect to the cartridge housing 402, driving the mixing stroke. FIG. 6(b) shows the device 400 after removal of the pin, after the medicament substances have been mixed. The remainder of the operating sequence of the device 400 is identical to that of the device 300 described above with reference to FIGS. 4 and 5.

Figure 7:
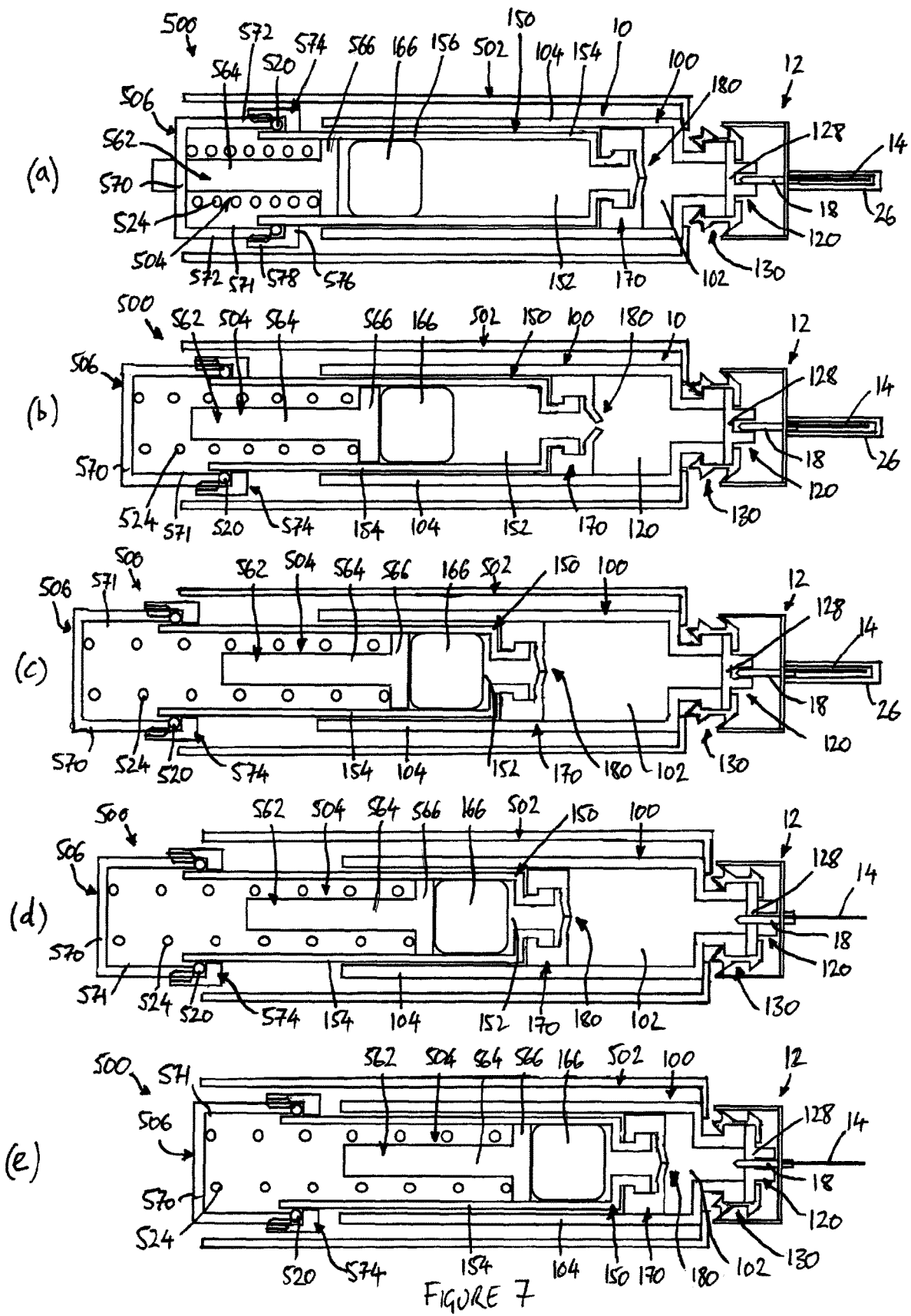
FIG. 7 shows schematic cross-sectional views of a sequence of steps during operation of the medicament cartridge of FIG. 1 when in use with a delivery device of a second type.

FIG. 7 illustrates, schematically, the cartridge 10 of FIGS. 1 and 2 in use with a delivery device 500 having a drive mechanism that operates using the second method described above, in which the stopper is directly driven during the mixing stroke to increase the pressure in the second chamber 152.

Referring to FIG. 7(a), the device 500 comprises a holder 502 for receiving and retaining the cartridge 10, a primary or mixing drive element 504 that is movable with respect to the holder 502 and the first and second container bodies 104, 154 to drive the mixing stroke of the second container 150, and a secondary or delivery drive element 506 that is coupled for joint axial movement with the second container body 154 and that is moveable with respect to the holder 502 to drive the delivery stroke of the second container 150. The holder 502 engages with the cartridge 10 in such a way that the first container 150 is fixed in position with respect to the holder 502.

The mixing drive element 504 comprises a plunger 562 having an elongate shaft 564 and an enlarged head 566 disposed at a distal end of the shaft 564. The head 566 of the plunger 562 is received in the bore of the major tubular part 156 of the second container body 154, on the proximal side of the stopper 166.

The plunger 562 is biased in the distal direction by a drive spring 524, a distal end of which acts on the head 566 of the plunger. A proximal end of the drive spring 524 acts on a button 570 that forms part of the delivery drive element 506. The button drive spring 524 is disposed around the shaft 564 of the plunger 562, and is accommodated in part in a plunger bore 571 that extends into the button 570 from its distal end.

A clamping arrangement is provided to secure the delivery drive element 506 to the second container body 154. The button 570 includes a generally tubular, distally extending wall 572 that has an externally threaded distal end region. A clamping collar 574 is disposed around the major tubular part 156 of the second container body 154, adjacent to its proximal end. The clamping collar 574 includes an annular base part 576 and a proximally-extending tubular wall 578 that is internally threaded to engage with the button 570.

A clamping ring 520, comprising an elastomeric O-ring, is disposed between the base part 576 of the clamping collar 574 and the distal end of the wall 572 of the button 570. The clamping ring 520 is sized to conform to the outer diameter of the tubular major part 156 of the second container body 154. During assembly of the device 500, the clamping collar 574 can be turned with respect to the button 570 to decrease the space between the base part 576 of the clamping collar 574 and the distal end of the wall 572 of the button 570, to squeeze the clamping ring 520 against the outer wall of the second container body 154. The radial clamping force thus applied by the clamping ring 520 to the second container body 154 locks the second container body 154 to the delivery drive element 506.

In an initial state of the device, shown in FIG. 7(a), the cartridge 10 is in its starting state, and the plunger 562 of the mixing drive element 504 is latched or otherwise held in an initial position with respect to the cartridge holder 502 with a suitable latch mechanism (not shown), with the drive spring 524 compressed. The needle assembly 12 is attached to the coupling element 130 in the first attachment position, in which the septum 128 of the closure member 120 is not pierced by the piercing member 18 of the needle assembly 12.

To mix the medicament substances, the latch mechanism is released to allow the plunger 562 to move in the distal direction with respect to the button 570 under the influence of the drive spring 524, displacing the stopper 166 in the distal direction with respect to the second container body 154. As shown in FIG. 7(b), the resulting pressure increase in the second chamber 152 causes the slit valve 180 to open. Driven by the pressure increase, the second medicament substance flows from the second chamber 152 to the first chamber 102 to mix with the first medicament substance. The second container body 154 moves proximally with respect to the first container body 104 to conserve the total combined volume of the first and second chambers 102, 152.

Thus, as in the previously-described examples, in this device 500 the second medicament container 150 moves proximally with respect to the first container 100 during the mixing stroke. This proximal movement results in the button 570 emerging from the proximal end of the holder 502.

At the end of the mixing stroke, the slit valve closes 180, as shown in FIG. 7(c). The first chamber 102 now contains the mixture of the first and second medicament substances. To ready the device 500 for delivery of the mixed medicament, the needle assembly 12 is moved into the second attachment position so that the piercing member 18 pierces the septum 128 and the needle cap 26 is removed, as shown in FIG. 7(d).

The mixed medicament in the first chamber 102 can then be expressed through the needle 14 by pushing the button 570 in the distal direction. This causes the second container 150 to move distally with respect to the first container 100 to reduce the volume of the first chamber 102 and release the medicament, as shown in FIG. 7(e).

Figure 8:
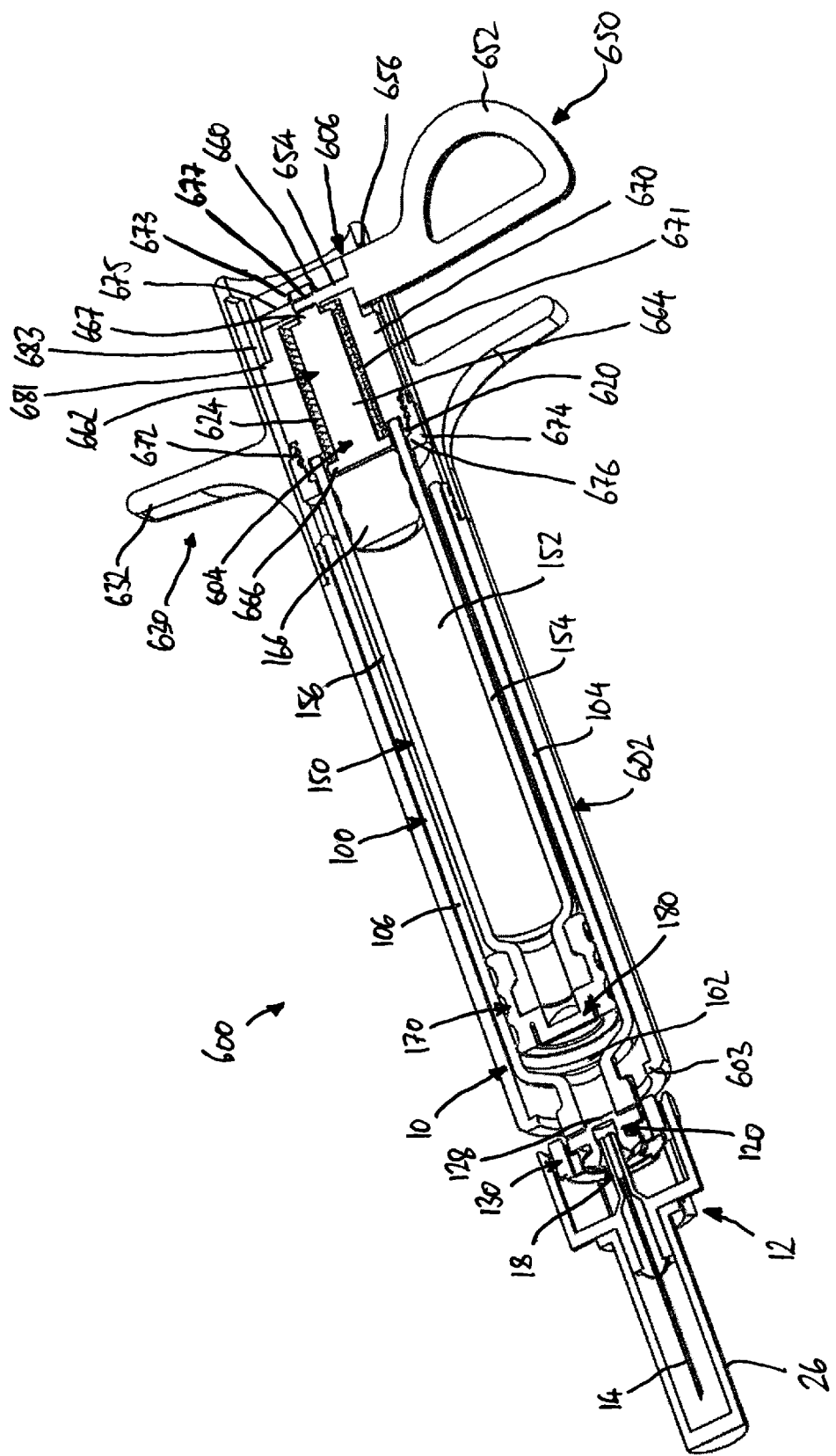
FIG. 8 shows a sectioned view of an embodiment of the delivery device of the second type in use with a medicament cartridge of the type shown in FIG. 1.

FIG. 8 shows an example of a device that operates on the principle described with reference to FIG. 7.

The device 600 is a manually-operated syringe in which the cartridge 10 and needle assembly 12 are identical to those described above with reference to FIGS. 4 and 5, and like reference numerals are used for like components in that regard.

The device 600 of FIG. 8 comprises a cartridge holder 602, which is provided with a retaining ring 603 at its distal end. The retaining ring 603 engages with the coupling element 130 of the cartridge 10 to apply an inwardly-directed retaining force to the coupling element 130 to clamp the coupling element 130 to the first container body 104 and to secure the cartridge 10 in a fixed position with respect to the cartridge holder 602. It should be noted that the clips of the coupling element 130 are not visible in the section shown in FIG. 8. A proximal end fitting 630, having a pair of finger tabs 632, is in threaded engagement with the proximal end of the cartridge holder 602.

As in the FIG. 7 device, the device 600 of FIG. 8 includes a mixing drive element 604 comprising a plunger 662 and a delivery drive element 606 comprising a button 670.

The delivery drive element 606 is fixed to the second container body by a clamping arrangement comprising a clamping collar 674 that is in threaded engagement with an externally-threaded distal end region 672 of the button 670, and an elastomeric O-ring or clamping ring 620. The clamping ring 620 is disposed around the major tubular part 156 of the second container body 154 and is located between a base part 676 of the clamping collar 674 and the distal end of the button 670. During assembly of the device 600, the clamping collar 672 can be turned with respect to the button 670 to squeeze the clamping ring 620 against the outer wall of the second container body 154, thereby to clamp the second container body 154 to the delivery drive element 606.

The plunger 662 has an elongate shaft 664 and an enlarged-diameter head 666 at a distal end of the shaft 664. The head 666 is received in the bore of the major tubular part 156 of the second container body 154, proximal to the stopper 166.

A drive spring 624 is disposed concentrically around the plunger shaft 664, in a plunger bore 671 of the button 670. The distal end of the drive spring 624 acts on the head 666 of the plunger 662, and the proximal end of the drive spring 624 acts on the button cap 670 at the proximal end of the plunger bore 671. The drive spring 624 thus biases the plunger 662 in the distal direction with respect to the button cap 670.

In a starting state of the device 600, as shown in FIG. 8, the plunger 662 is latched to the button cap 670 by a latching arrangement that comprises a user-removable tab 650 that is similar to the tab 450 of the device of FIG. 6 as described above.

In the FIG. 8 device 600, an elongate latching rod 667 projects proximally from the plunger shaft 664 and locates in a cylindrical recess 673 formed at the proximal end of the plunger bore 671 of the button 670. Both the button 670 and the latching rod 667 are provided with diametrically-extending bores 675, 677. When in the initial position, the bore 677 of the latching rod 667 is aligned with the bore 675 of the button 670, and an elongate pin 654 of the tab 650 extends through both bores 675, 677 to latch the plunger 662 in the initial position, with the drive spring 624 compressed. An annular ridge or detent 660 is provided on the pin 654 to locate in a recess where the bores 675, 677 of the button 670 and the latching rod 667 meet, so that removal of the tab 650 requires a minimum threshold force to be applied.

An aperture 656 is provided in the cartridge holder 602 to accommodate the tab 650 when in place, and the button 670 is provided with longitudinally-extending ribs 681 that cooperate with corresponding recesses 683 in the cartridge holder 602 to ensure that the bore 675 of the button 670 is correctly aligned with the aperture 656 during assembly of the device.

Operation of the device 600 follows the same steps as described with reference to the device 500 shown in FIG. 7. To start the mixing stroke of the device 600, the handle part 652 of the tab 650 can be pulled to remove the pin 654 from the bores 675, 677, thus releasing the plunger 662 for movement in the distal direction with respect to the button 670, and pushing the stopper 166 in the distal direction to reduce the volume of the second chamber 152 of the cartridge 10, and the second container body 154 moves in the proximal direction to increase the volume of the first chamber 102 accordingly. The second medicament substance flows through the slit valve 180 into the first chamber 102 to mix with the first medicament substance.

The proximal movement of the second container body 154 causes the button 670 to move from an initial, retracted position to an operating position in which the button 670 has emerged from the proximal end of the end fitting 630 of the device 600. Thus, at the end of the mixing stroke, the slit valve 180 closes, and the needle assembly 12 can be moved the second attachment position so that the piercing member 18 pierces the septum 120 of the first closure member 120. The needle cap 26 can be removed, and the button 670 can be depressed to move the second container body 154 back in the distal direction in the delivery stroke of the device 600 to express the medicament from the first chamber 102 through the needle 14.

From the above, it will be appreciated that the cartridge of the present invention is suitable for use with delivery devices of several different types, including disposable syringes, safety syringes, injection pens, auto-injectors, pumps, infusion sets and so on. The provision of a coupling element at the distal end of the cartridge allows the cartridge to be clipped or otherwise secured to a suitable device. For example, the cartridge can be used with a medicament delivery device or an adaptor device for a medicament delivery device, and the coupling element may couple to a needle assembly, housing, cartridge holder, adaptor cap or other component of such a medicament delivery device or adaptor device. Thus, mixable medicament substances can be validated and approved for use with the cartridge of the invention to allow their use across a range of different devices to suit particular clinical situations or user preferences.

Use of the cartridge is not limited to devices of the types shown in FIGS. 4 to 6 and FIG. 8, in which the delivery stroke is driven manually by the user applying a driving force to a button that is connected directly to the second container body. Instead, any suitable means could be used to drive the delivery stroke of the device.

As explained above, in the illustrated examples, the delivery stroke is driven by distal movement of a drive element associated with the second container (i.e. the single mixing drive element in the case of a device that operates in accordance with the "negative pressure" principle of FIG. 3, or the delivery drive element in the case of a device that operates in accordance with the "positive pressure" principle of FIG. 7) after the mixing stroke is complete. Any suitable mechanism could be provided to drive distal movement of the drive element. In particular, in an auto-injector type device, a suitable delivery drive means, such as a delivery spring, could be provided to bias the drive element in the distal direction, and the drive element could be latched in position with a suitable latch arrangement. When triggered, the latch arrangement could release the drive element to perform the delivery stroke. The drive element could itself comprise a spring or other biasing means for direct engagement with the second container.

The device could be arranged so that the delivery stroke is triggered automatically at the end of the mixing stroke. Alternatively, the mixing stroke and the delivery stroke could be triggered by separate user actions performed sequentially. Further automatic or user-triggered steps, such as needle insertion, needle retraction and/or needle shrouding could be incorporated into the device.

The cartridge is also suitable for use with re-usable delivery devices, such as injection pens, medicament pumps, infusion devices and so on. For this purpose, the cartridge may be fitted with an adaptor assembly or device to adapt the cartridge for use with a medicament delivery device having a conventional plunger mechanism in which a plunger is displaced in the distal direction to deliver a pre-determined or selectable dose.

Figure 9:
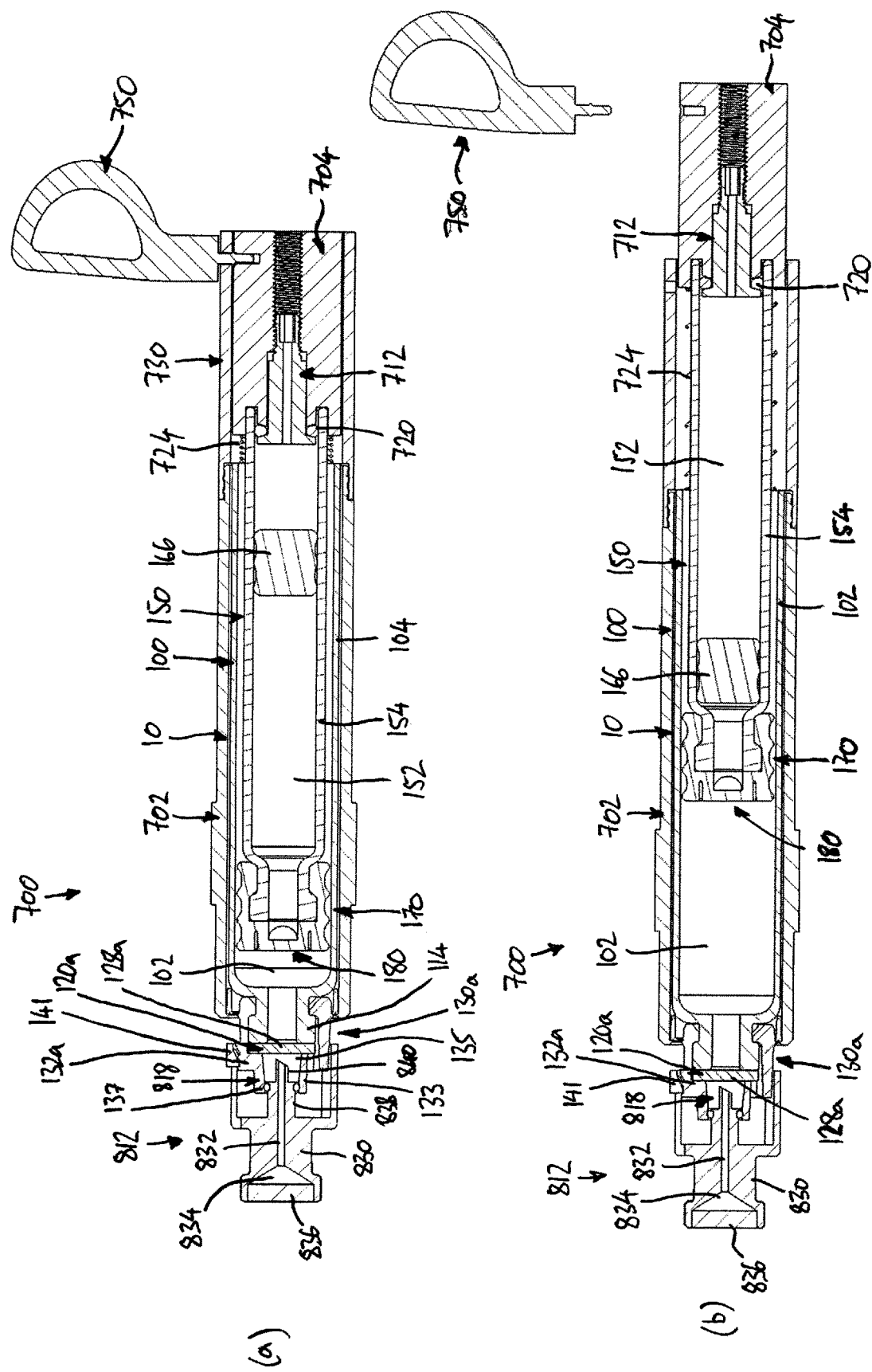
FIG. 9 shows cross-sectional views of a medicament cartridge of the type shown in FIG. 1 in use with an adaptor device.

FIG. 9 illustrates the cartridge 10 in use with such an adaptor device 700. In place of the needle assembly 12 of previous examples, the adaptor device 700 is provided with an adaptor cap 812 at its distal end.

The adaptor cap 812 comprises an adaptor body 830 which is provided with an axial passage 832. The passage 832 opens at its distal end into a chamber 834. The distal side of the chamber 834 is closed by a pierceable elastomeric septum 836. The septum 836 may be held in place by a suitable crimp or other attachment means (not shown). The proximal end of the passage 832 extends through a generally tubular piercing member 818 having an enlarged diameter tubular boss 838 and a reduced-diameter tip part 840.

The piercing member 818 is arranged to engage with a modified coupling element 130*a* and closure member 120*a* of the cartridge 10. In this case, the closure member 120*a* comprises a flat elastomeric disc that defines the septum 128*a* that closes the distal end of the first chamber 102 of the cartridge 10.

The annular body 132*a* of the coupling element 130*a* is provided with a tubular throat 133 that is integrally formed with the coupling element 130*a* and defines a generally frustoconical bore 135. With the coupling element 130*a* clipped in place on the distal end of the first container body 104, the proximal end of the throat 133 presses against the closure member 120*a* to seal the closure member 120*a* against the distal end of the collar 114.

The bore 135 of the throat 133 is arranged to receive the piercing member 818 of the adaptor cap 812. An O-ring 137 is retained in an annular groove 139 that is disposed adjacent to the proximal end of the boss 838. In this way, when the adaptor cap 812 is arranged in the first attachment position with respect to the first container body 104, a seal is formed by the O-ring 137 between the throat 133 of the coupling element 130*a* and the boss 838. The proximal end of the piercing member 818, along with the passage 832 and the chamber 834, are therefore kept sterile while the adaptor cap 812 is in the first attachment position. Clip formations 141 (only one of which is shown in FIG. 9(*a*)) are provided on the adaptor body 830 to engage with corresponding engagement formations on the annular body 132*a* of the coupling element 130*a*.

The cartridge 10 is retained in a generally tubular cartridge holder 702 of the adaptor device 700. The distal end of the cartridge holder 702 is shaped to engage with the coupling element 130*a* of the cartridge 10 to fix the first container body 104 in position with respect to the cartridge holder 702. A distal end fitting 730 is in threaded engagement with the cartridge holder 702.

The adaptor device 700 is provided with a drive element 704, a clamping rod 712 and clamping ring 720 for securing the drive element 704 of the second container body 154, a drive spring 724 for biasing the drive element 704 in the proximal direction with respect to the first container body 104, and a user-removable tab 750 for latching the drive element 704 in its initial position with respect to the cartridge holder 702. These components are substantially identical in structure to and function in the same way as the equivalent components in the devices of FIGS. 4, 5 and 6, and so will not be described in further detail.

The cartridge 10, together with the adaptor device 700, can be supplied in an initial condition as shown in FIG. 7(*a*), with the adaptor cap 812 in the first attachment position and the tab 750 in place to latch the drive element 704 in its initial position. The first and second medicament substances are kept sterile and separated in the first chamber 102 and the second chamber 152 respectively.

When it is desired to install the cartridge 10 and the adaptor device 700 in a medicament delivery device, the tab 750 can be removed from the assembly 700, allowing the drive element 704, and hence the second container body 152, to move proximally with respect to the first container body 104 under the influence of the drive spring 724, as shown in FIG. 9(b). Thus the mixing stroke is performed before the cartridge 10 and adaptor device 700 are installed in the delivery device.

It will be appreciated from FIG. 9(b) that, at the end of the mixing stroke, the cartridge 10 and adaptor device 700 can be considered to be functionally equivalent to a conventional injection pen or pump cartridge, with the now-mixed medicament disposed in the first chamber 102. Thus the adaptor cap 812 is arranged to accept a disposable needle or other cannula connector (not shown), with the septum 836 of the adaptor cap 812 being pierced by a proximal end of the needle or by a further piercing member. Once the adaptor cap 812 has been moved to its second attachment position, so that the piercing member 818 opens the septum 128a of the cartridge 10, the mixed medicament can flow from the first chamber 102 through the passage 832 in the adaptor to the attached needle or cannula. The clip formations 141 are arranged to engage the proximal end of the annular body 132a of the coupling element 130a when the adaptor cap 812 is in the second attachment position.

Once installed in the device, the second container 150, together with the drive element 704, the second closure member 170 and the closed slit valve 180 able to act together as a piston element that can be driven in the distal direction by a plunger or other drive member of the delivery device to express the mixed medicament from the first chamber 102 through the needle or cannula attached to the adaptor cap 812.

It will be appreciated that the adaptor cap 812 shown in FIG. 9, or modifications and variants thereof, could also be used in place of the needle assembly 12 in the examples of FIGS. 1 to 8.

Figure 10:
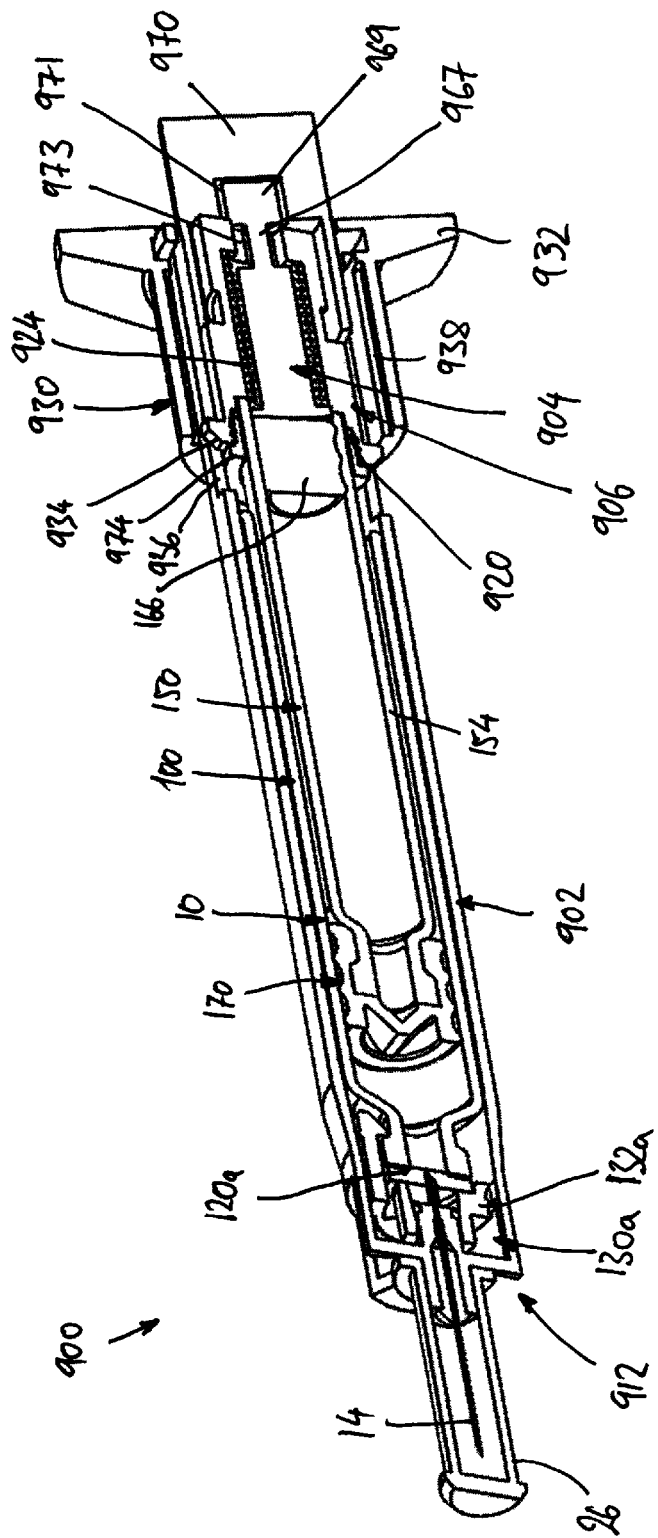
FIG. 10 is a sectioned view of another embodiment of the delivery device of the second type in use with a medicament cartridge of the type shown in FIG. 1.

For example, FIG. 10 shows an example of a device 900 having a needle assembly 912 that is similar to the adaptor cap 812 described above with reference to FIG. 9, in use with a cartridge 100 having the modified coupling element 130a and septum 120a also shown in FIG. 9. The device 900 comprises a manually-operated syringe that is based on the principle described with reference to FIGS. 7 and 8.

The device 900 of FIG. 10 includes a cartridge holder 902, and the needle assembly 912 is integrated with the cartridge holder 902. The cartridge 10 is secured in a fixed position with respect to the cartridge holder 902. A proximal end fitting 930, having a pair of finger tabs 932, is disposed at the proximal end of the cartridge holder 902.

In this case, the end fitting 930 is arranged concentrically around the proximal end of the cartridge holder 902, and is turnable with respect to the cartridge holder 902 about the long axis of the device 900 in order to release the mixing drive element 904 of the device 900 as will be described in more detail below.

As in the FIG. 8 device, the mixing drive element 904 is in the form of a plunger 962, and a delivery drive element 906 is fixed to the second container body 152 by a clamping arrangement comprising a clamping collar 974 and an elastomeric clamping ring 920. The mixing drive element 904 is biased in the distal direction with respect to the delivery drive element 906 by a drive spring 924.

The delivery drive element 906 is guided for axial movement with respect to the cartridge holder 902 by a pair of outwardly-projecting guide elements 934. Each of the guide elements 934 engages with a longitudinally-extending slot 936 in the cartridge holder 902. In the initial, unmixed state of the device 900, the guide elements 934 are disposed on the distal side of the end fitting 930, and the end fitting 930 blocks movement of the guide elements 934, and therefore the delivery drive element 906, in the proximal direction. When the end fitting 930 is turned with respect to the cartridge holder 902 to release the mixing drive element 904, a pair of longitudinally-extending channels 938 formed on the inner surface of the end fitting 930 move into alignment with the slots 936 to accommodate the guide elements 934, thereby allowing proximal movement of the delivery drive element 906 with respect to the cartridge holder 902.

The mixing drive element 904 is coupled to the delivery drive element 906 by a latching member 967. The latching member 967 has an enlarged head portion 969 with a flattened, generally oblong cross section. The latching member 967 extends proximally through an oblong aperture 973 at the proximal end of the delivery drive element 906.

The head portion 969 of the latching member 967 extends into a recess 971 in a button 970 disposed at the proximal end of the device 900. The button 970 is retained by the delivery drive element 906 so that the button 970 and the delivery drive element 906 are coupled for joint axial movement with respect to the cartridge holder 902. The button 970 is keyed to the end fitting 930 so that turning movement of the end fitting 930 with respect to the cartridge holder 902 causes turning movement of the button 970 with respect to the delivery drive member 906.

In a starting state of the device 900, the end fitting 930 is positioned in a first angular orientation with respect to the cartridge holder 902, as shown in FIG. 10. In this state, the head portion 969 of the latching member 967 is held in an angularly offset position with respect to the aperture 973 by the button 970, so that the head portion 969 cannot pass through the aperture 973.

Figure 11:
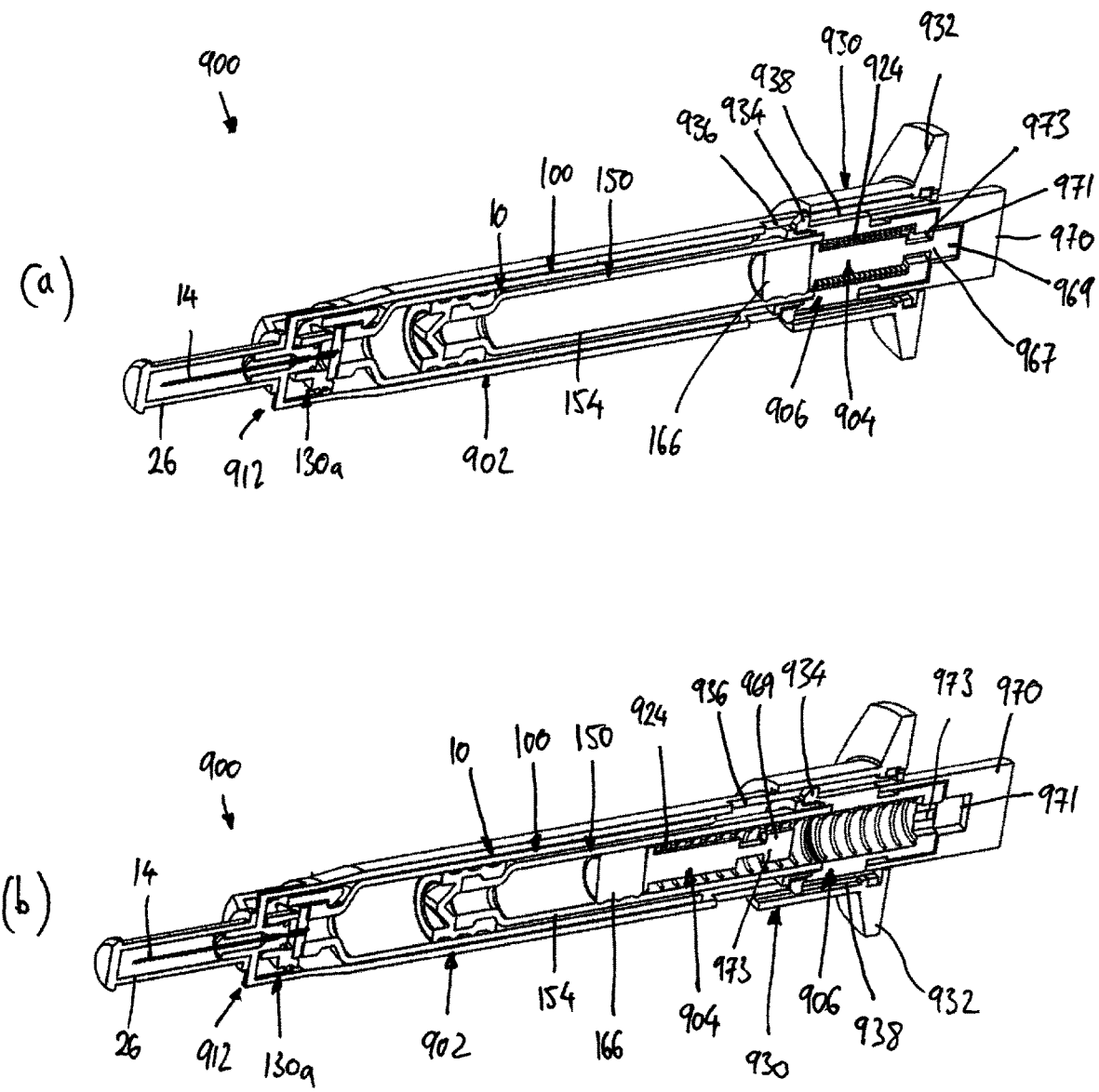
FIG. 11 shows sectioned views of the delivery device of FIG. 10.

To operate the device 900, the end fitting 930 is turned with respect to the cartridge holder 902 to a second angular orientation, as shown in FIG. 11(a). The turning movement of the end fitting 930 causes turning movement of the button 970, which in turn causes the head portion 969 of the latching member 967 to become angularly aligned with the aperture 973 in the delivery drive element 906. At the same time, the channels 938 in the end fitting 930 align with the guide formations 934 of the delivery drive element 906.

Now, the head portion 969 of the latching member 967 can pass through the aperture 973, releasing the mixing drive element 904 for distal movement to perform the mixing stroke of the device 900, as shown in FIG. 11(b). As in the embodiment of FIG. 8, as the stopper 166 is displaced in the distal direction, the second container body 154 moves in the proximal direction to cause the button 970 to move into a proximally extended position, and the button 970 can be subsequently depressed to perform a delivery stroke of the device 900 as previously described.

In another device arrangement (not shown), the second container body 154 is held in place with respect to the cartridge housing during the mixing stroke, and the first container body 104 is moved distally with respect to the cartridge housing. In this case, a mixing spring may be provided to bias the first container body 104 in the distal direction with respect to the cartridge housing, and a latch mechanism may be provided for preventing movement of the first container body 104 until the latch mechanism is activated to release the first container body 104. Distal movement of the first container body 104 with respect to the second container body 154 then increases the volume of the first chamber 102, causing a drop in pressure in the first chamber 102 that drives mixing of the first and second substances as previously described. In this arrangement, the mixing spring may act as the mixing element.

The second container 150 may be held in place during the mixing stroke by a holding member that is attached to the second container 150, for example by a clamping arrangement of the type previously described. The holding member may function as a delivery drive element. For instance, the device could be configured as an auto-injector, in which case the holding member may be latched with respect to the cartridge holder, and the delivery stroke can be actuated by delatching the holding member to drive the second container 150 in the distal direction.

It will be understood that the cartridge of the present invention could be used with any delivery device, adaptor device or other apparatus, device or component having a piercing member that can be coupled to the coupling element of the cartridge in such a way that the septum is pierced by the piercing member upon attachment. In some variants, the piercing member comprises a proximal end of a hypodermic needle, and in further variants the septum of the cartridge is replaced with a valve or other sealing element, and a suitable sealing element release member or valve opening member is used in place of the piercing member.

Although it is preferable that the needle assembly, adaptor cap or similar component is attachable to the cartridge to define a first attachment position in which the sealing element remains intact and a second attachment position in which the sealing element is opened, this is not essential. Instead, an attachable needle assembly, adaptor cap or similar component could remain separated from the cartridge 10 until it is necessary to open the sealing element, and then attached to the cartridge 10 at that time to open the sealing element with the sealing element release member.

It is also conceivable that the sealing element may be designed to open in response to an increase in pressure of the medicament in the first chamber when the second container is moved towards the distal end of the cartridge in the delivery stroke, in which case a sealing element release member is not required. For example, a self-opening valve component of this type may comprise a slit valve that is similar to the slit valve used to seal the distal end of the second chamber in the illustrated examples.

The needle assembly, adaptor cap or other device component may be a separate, attachable component of a delivery device or adaptor device, or may be integral with or otherwise coupled to the delivery device or the adaptor device.

Many further variations and modifications of the cartridge itself are also possible. For example, although not illustrated, an additional seal may be provided between the first and second container bodies, for example at the proximal end of the first container body. This additional seal maintains the sterility of the annular space between the first and second container bodies on the proximal side of the second closure member. Conveniently, the additional seal may be an annular ring of elastomeric material, such as an O-ring, that is squeezed between the inner surface of the first container body and the outer surface of the second container body. Upon movement of the second container body in the proximal direction, the additional seal may "blow out" as the volume of the annular space decreases.

Several alternatives for the slit valve that closes the distal end of the second chamber can be contemplated. For instance, the valve could be in the form of a duckbill valve, flap valve, umbrella valve, cross-slit valve or any other suitable valve formation, including known one-way or check valve arrangements. In general terms, the valve means may comprise any suitable closure for preventing mixing of the first and second substances before the mixing stroke. Thus, in a further example, the valve means comprises a membrane that is used to close the distal end of the second chamber. In this case, the membrane may detach, split or rupture when a sufficient pressure difference is applied across the membrane to open the distal end of the second chamber.

It will be appreciated that, in some embodiments, the valve means or closure that separates the first and second containers may not re-close at the end of the mixing stroke.

The first closure member and the coupling element can also take different forms to those illustrated. For example, the first closure member may comprise a bung that is disposed in the distal end of the first container body, or a cap that is fitted over the distal end of the first container body. The coupling element may be moulded or otherwise attached to the first closure member or to the first container body.

The coupling element may be provided with any suitable engagement formations to allow the cartridge to be coupled with a cartridge connector part of a delivery device, needle assembly, adaptor cap or other device, including clips, ridges, protrusions, recesses, and so on, which can be configured for engagement with corresponding formations on the cartridge connector.

The present invention has been devised primarily for use with reconstitutable medicaments, in which the first medicament substance is a solid (such as a lyophilised medicament) and the second medicament substance is a liquid (such as a diluent for rehydrating the solid), the invention is not limited to use with such medicaments. The cartridge could for example be used to store and mix two liquid medicament substances. Either or both of the medicament substances could conceivably be in other forms including gels, suspensions, colloids, sols, and so on.

The cartridge of the present invention can also be readily adapted for use as a package for a single-component medicament, by replacing the second container, including the second closure member, the valve means and the stopper, with a suitable stopper or other piston element that is sized to seal against the inner surface of the major tubular part of the first container body. The coupling arrangement at the distal end of the first container body is preserved, so that devices that are arranged for use with the cartridge of the invention can be easily re-configured for the delivery of a single-component medicament.

Further modifications and variations of the above-described examples are also possible without departing from the scope of the present invention as defined by the appended claims.

The invention claimed is:

1. A device for mixing first and second substances in a cartridge comprising a first container having a first chamber for storage of the first substance, an outlet disposed at a distal end of the first chamber, a closure member for closing the outlet, a second container at least partially received in the first container and having a second chamber for storage of the second substance, a valve for closing a distal end of the second chamber and a proximal end of the first chamber, and a stopper for closing a proximal end of the second chamber, the stopper being movable with respect to the second container, the device comprising:
- a cartridge holder for receiving the cartridge;
- a mixing drive element;
- a delivery drive element; and
- an operating mechanism comprising a spring for driving movement of the mixing drive element in a distal direction with respect to the cartridge holder upon activation of the operating mechanism, thereby to cause relative movement between the first container and the second container and to displace the second substance into the first chamber through the valve when the outlet is closed to cause mixing of the first and second substances in a mixing stroke of the device;
- wherein the second container, in response to actuation of the delivery drive element, moves in a distal direction with respect to the first container when the outlet is open to displace the mixed first and second substances through the outlet in a delivery stroke of the device,
- wherein movement of the mixing drive element in the distal direction causes proximal movement of the second container with respect to the cartridge holder, and
- wherein the proximal movement of the second container during the mixing stroke of the device causes movement of the delivery drive element from an initial position into an operating position disposed proximally with respect to the initial position.

2. The device according to claim 1, wherein the mixing drive element is arranged to displace the stopper of the cartridge in a distal direction with respect to the second container during the mixing stroke.

3. The device according to claim 2, wherein the mixing drive element comprises a plunger.

4. The device according to claim 1, wherein the delivery drive element comprises a button.

5. The device according to claim 1, wherein the delivery drive element is attachable to the second container of the cartridge.

6. The device according to claim 5, further comprising a clamp arrangement for securing the delivery drive element to the second container.

7. The device according to claim 6, wherein the clamp arrangement is arranged to apply a clamping force to an outer wall of the second container.

* * * * *